(12) United States Patent
Kim et al.

(10) Patent No.: US 10,550,168 B2
(45) Date of Patent: *Feb. 4, 2020

(54) COMPOSITION FOR TREATING DIABETES OR DIABESITY COMPRISING OXYNTOMODULIN ANALOG

(71) Applicant: HANMI PHARM. CO., LTD., Hwaseong-si, Gyeonggi-do (KR)

(72) Inventors: Jin Sun Kim, Yongin-si (KR); Dae Jin Kim, Hwaseong-si (KR); Sang Hyun Lee, Seoul (KR); Sung Youb Jung, Suwon-si (KR); Se Chang Kwon, Seoul (KR)

(73) Assignee: Hanmi Pharm. Co., Ltd., Hwaseong-si, Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/960,205

(22) Filed: Apr. 23, 2018

(65) Prior Publication Data

US 2018/0237490 A1    Aug. 23, 2018

Related U.S. Application Data

(62) Division of application No. 14/440,653, filed as application No. PCT/KR2013/009990 on Nov. 6, 2013, now abandoned.

(30) Foreign Application Priority Data

Nov. 6, 2012 (KR) .................... 10-2012-0124724

(51) Int. Cl.
| | | |
|---|---|---|
| A61K 38/22 | (2006.01) | |
| A61K 38/26 | (2006.01) | |
| C07K 14/575 | (2006.01) | |
| C07K 14/605 | (2006.01) | |
| C07K 16/00 | (2006.01) | |
| C07K 16/30 | (2006.01) | |
| A61K 47/64 | (2017.01) | |

(52) U.S. Cl.
CPC ............ *C07K 14/575* (2013.01); *A61K 38/22* (2013.01); *A61K 47/643* (2017.08); *A61K 47/6435* (2017.08); *C07K 14/605* (2013.01); *C07K 16/00* (2013.01); *C07K 16/3046* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 6,776,983 B1 | 8/2004 | Sumida et al. | |
| 7,217,845 B2 | 5/2007 | Rosen et al. | |
| 7,521,424 B2 | 4/2009 | Rosen et al. | |
| 7,737,260 B2 | 6/2010 | Kim et al. | |
| 7,928,058 B2 | 4/2011 | Sinha et al. | |
| 8,263,084 B2 | 9/2012 | Song et al. | |
| 8,729,017 B2 | 5/2014 | DiMarchi et al. | |
| 8,778,872 B2 | 7/2014 | DiMarchi et al. | |
| 8,975,001 B2 | 3/2015 | Bae | |
| 9,522,946 B2 | 12/2016 | Jung et al. | |
| 9,527,898 B2 * | 12/2016 | Jung .................... C07K 14/605 |
| 9,724,420 B2 * | 8/2017 | Kim .................... A61K 9/0019 |
| 9,731,031 B2 | 8/2017 | Jung et al. | |
| 2003/0032588 A1 | 2/2003 | Marshall et al. | |
| 2004/0087778 A1 | 5/2004 | Feige et al. | |
| 2006/0269553 A1 | 11/2006 | Kim et al. | |
| 2009/0053246 A1 | 2/2009 | Kim et al. | |
| 2009/0238838 A1 | 9/2009 | Kim et al. | |
| 2009/0298757 A1 | 12/2009 | Bloom et al. | |
| 2010/0144617 A1 | 6/2010 | Sinha Roy et al. | |
| 2010/0190701 A1 | 7/2010 | Day et al. | |
| 2010/0196405 A1 | 8/2010 | Ng | |
| 2010/0330108 A1 | 12/2010 | Song et al. | |
| 2011/0034374 A1 | 2/2011 | Bloom et al. | |
| 2011/0065633 A1 | 3/2011 | DiMarchi et al. | |
| 2011/0152182 A1 | 6/2011 | Alsina-Fernandez et al. | |
| 2011/0190200 A1 | 8/2011 | DiMarchi et al. | |
| 2012/0003712 A1 | 1/2012 | Song et al. | |
| 2012/0165503 A1 | 6/2012 | Carrington et al. | |
| 2012/0178670 A1 | 7/2012 | Riber et al. | |
| 2012/0329707 A1 | 12/2012 | DiMarchi et al. | |
| 2013/0035285 A1 | 2/2013 | Lau et al. | |
| 2013/0122023 A1 | 5/2013 | Woo et al. | |

FOREIGN PATENT DOCUMENTS

| | | |
|---|---|---|
| CN | 101213209 A | 7/2008 |
| CN | 101389648 A | 3/2009 |

(Continued)

OTHER PUBLICATIONS

US 8,729,011 B2, 05/2014, DiMarchi (withdrawn)

(Continued)

*Primary Examiner* — Julie Ha
*Assistant Examiner* — Kristina M Hellman
(74) *Attorney, Agent, or Firm* — BakerHostetler

(57) ABSTRACT

Disclosed are a composition for preventing or treating diabetes, disbesity or diabetic complications, containing an oxyntomodulin analog as an active ingredient and a method for treating diabetes, diabesity or diabetic complications, including administering a pharmaceutically effective amount of an oxyntomodulin analog to a subject. The oxyntomodulin analog shows a greater activity to activate a GLP-1 receptor and a glucagon receptor, than native oxyntomodulin. The oxyntomodulin analog induces an expansion of beta-cells and increases insulin secretion, thereby reducing blood glucose levels that were increased due to a high-calorie and high-fat diet. The oxyntomodulin analog induces decreases in a body weight and appetite to improve insulin sensitivity and is useful in maintaining normal blood glucose levels.

10 Claims, 4 Drawing Sheets

Specification includes a Sequence Listing.

(56) References Cited

FOREIGN PATENT DOCUMENTS

| | | |
|---|---|---|
| CN | 101578107 A | 11/2009 |
| CN | 101974077 A | 2/2011 |
| CN | 102010473 A | 4/2011 |
| CN | 102369209 A | 3/2012 |
| CN | 103732616 A | 4/2014 |
| CN | 103732618 A | 4/2014 |
| EP | 2300037 A2 | 3/2011 |
| EP | 2330124 A2 | 6/2011 |
| EP | 1891105 B1 | 4/2012 |
| EP | 2884994 A1 | 6/2015 |
| JP | 2003-531632 A | 10/2003 |
| JP | 2008-543816 A | 12/2008 |
| JP | 2009-527558 A | 7/2009 |
| JP | 2009-203235 A | 9/2009 |
| JP | 2011-505355 A | 2/2011 |
| JP | 2011-511753 A | 4/2011 |
| JP | 2013-537525 A | 10/2013 |
| KR | 10-0389726 B1 | 6/2003 |
| KR | 10-2005-0026685 A | 3/2005 |
| KR | 10-2006-0106486 A | 10/2006 |
| KR | 10-2008-0039375 A | 5/2008 |
| KR | 10-2009-0096498 A | 9/2009 |
| KR | 10-2009-0098843 A | 9/2009 |
| KR | 10-0925017 B1 | 11/2009 |
| KR | 10-2010-0105494 A | 9/2010 |
| KR | 10-2011-0039230 A | 4/2011 |
| KR | 10-2011-0056472 A | 5/2011 |
| KR | 10-2012-0043208 A | 5/2012 |
| KR | 10-2012-0052973 A | 5/2012 |
| KR | 10-2012-0137271 A | 12/2012 |
| KR | 10-2012-0139579 A | 12/2012 |
| NZ | 618811 A | 5/2016 |
| NZ | 718999 A | 7/2017 |
| TW | 200848423 A | 12/2008 |
| TW | 201245246 | 11/2012 |
| TW | 201546053 | 12/2015 |
| WO | 96/32478 A1 | 10/1996 |
| WO | 97/34631 A1 | 9/1997 |
| WO | 2003/022304 A1 | 3/2003 |
| WO | 2004/062685 A2 | 7/2004 |
| WO | 2005/035761 A1 | 4/2005 |
| WO | 2005/087797 A1 | 9/2005 |
| WO | 2006/059106 A2 | 6/2006 |
| WO | 2006/086769 A2 | 8/2006 |
| WO | 2006/107124 A1 | 10/2006 |
| WO | 2006/134340 A2 | 12/2006 |
| WO | 2007/022123 A2 | 2/2007 |
| WO | 2007/100535 A2 | 9/2007 |
| WO | 2007/146038 A2 | 12/2007 |
| WO | 2008/071972 A1 | 6/2008 |
| WO | 2008/082274 A1 | 7/2008 |
| WO | 2008/101017 A2 | 8/2008 |
| WO | 2009/033756 A2 | 3/2009 |
| WO | 2009/058734 A1 | 5/2009 |
| WO | 2009/069983 A2 | 6/2009 |
| WO | 2009/099763 A1 | 8/2009 |
| WO | 2009/155257 A1 | 12/2009 |
| WO | 2009/155258 A2 | 12/2009 |
| WO | 2013/192129 A1 | 12/2009 |
| WO | 2010/013012 A2 | 2/2010 |
| WO | 2010/033207 A1 | 3/2010 |
| WO | 2010/033220 A2 | 3/2010 |
| WO | 2010/070253 A1 | 6/2010 |
| WO | 2010/071807 A1 | 6/2010 |
| WO | 2010/096052 A1 | 8/2010 |
| WO | 2010/096142 A1 | 8/2010 |
| WO | 2010/107256 A2 | 9/2010 |
| WO | 2010/108153 A2 | 9/2010 |
| WO | 2010/148089 A1 | 12/2010 |
| WO | 2011/006497 A1 | 1/2011 |
| WO | 2011/056713 A2 | 5/2011 |
| WO | 2011/071957 A1 | 6/2011 |
| WO | 2011/075393 A2 | 6/2011 |
| WO | 2011/087671 A1 | 7/2011 |
| WO | 2011/087672 A1 | 7/2011 |
| WO | 2011/143208 A1 | 11/2011 |
| WO | 2011/163012 A2 | 12/2011 |
| WO | 2012/011752 A2 | 1/2012 |
| WO | 2012/057525 A2 | 5/2012 |
| WO | 2012/088379 A2 | 6/2012 |
| WO | 2012/169798 A2 | 12/2012 |
| WO | 2012/173422 A1 | 12/2012 |
| WO | 2013/157002 A1 | 10/2013 |
| WO | 2014/049610 A2 | 4/2014 |
| WO | 2014/073842 A1 | 5/2014 |
| WO | 2014/073845 A1 | 5/2014 |

OTHER PUBLICATIONS

Berger et al., "The Effect of Treatment of Type 2 (Insulin Independent) Diabetes Meilitus on Plasma Concentrations of Pancreatic Polypeptide and Glucagon," Diabetologia 21:120-125 (1981). (Year: 1981).*
Zhou et al., "Role of AMP-activated protein kinase in mechanism of metformin action", J. Clinical Invest., 2001, 108, 1167-1174.
Wynne et al., "Oxyntomodulin increases energy expediture in addition to decreasing energy intake in overweight and obese humans: a randomised controlled trial," International Journal of Obesity, 2006, 30, 1729-1736.
Wynne et al, "Subcutaneous Oxyntomodulin Reduces Body Weight in Overweight and Obese Subjects a Double-Blind, Randomized, Controlled Trial", Diabetes, Aug. 2005, vol. 54, pp. 2390-2395.
World Health Organization, Global Strategy on Diet, Physical Activity and Health, 2004.
What Causes Overweight and Obesity?, from http://www.nhlbi.nih.gov/health/health-topics/topics/obe/causes.html, pp. 1-5, accessed Oct. 6, 2014.
Water, from http://www.biology-online.org/dictionary/Water, pp. 1-3, accessed Apr. 24, 2014.
Voet et al., "Abnormal Hemoglobins", Biochemistry, John Wiley & Sons Inc., 1995, 235-241.
Vitamins & Supplements Search, http://www.webmd.com/vitamins-supplements/condition-1275-Hyperlipidemia.a- spx, accessed Dec. 29, 2015, pp. 1-3.
Treethammathurot et al., "Effect of PEG molecular weight and linking chemistry on the biological activity and thermal stability of PEGylated trypsin", International Journal of Pharmaceutics, 2008, vol. 357, pp. 252-259.
Sigma-Aldrich, "Exendin-4 sequence", http://www.simgaaldrich.com/catalog/product/sigma/e7144lang=en®ion=US, accessed Dec. 28, 2015, 1 page.
Shigeru, "Obesity and Metabolic Syndrome", Tokyo Internal Medical Association Seminar 2008 Special Lecture, Dec. 2008, vol. 24, No. 2, 8 pages.
Shani Ben-Shlomo et al., "Glucagon-like pepetide-1 reduces hepatic lipogenesis via activation of AMP-activated protein kinase", Journal of Hepatology, Sep. 27, 2010, vol. 54, No. 6, pp. 1214-1223.
Seok et al., "Exendin-4 Improves Nonalcoholic Fatty Liver Disease by Regulating Glucose Transporter 4 Expression in ob/ob Mice", Korean Journal of Physiology and Pharmacology, Jan. 1, 2014, p. 333.
Santoprete et al., "DPP-IV-resistant, long acting oxyntomodulin derivatives", Journal of Peptide Science, Feb. 2011, vol. 17, No. 4, 270-280.
Rudinger, "Characteristics of the amino acids as components of a peptide hormone sequence", Peptide Hormones, JA Parsons Ed., 1976, pp. 1-7.
Pocai et al., "Glucagon-like peptide 1/glucagon receptor dual agonism reverses obesity in mice", Diabetes, 2009, vol. 58, No. 10, 2253-2266.
Obesity Causes, from http://www.hsph.harvard.edu/obesity-prevention-source/obesity-causes/, pp. 1-3, accessed Oct. 6, 2014.
Ngo et al, Computational Complexity, Protein Structure Protection, and the Levinthal Paradox, 1994, pp. 491-494.
Neuschwander-Tetri et al., "Improved Nonalcoholic Steatohepatitis After 48 Weeks of Treatment With the PPAR-y Ligand Rosiglitazone", Hepatology, 2003, 38, 1008-1017.

(56) References Cited

OTHER PUBLICATIONS

Merriam Webster, Dictionary: prophylactic, (3 pages total), accessed from the WWW on Feb. 8, 2015. (3pgs.) URL: http://www.merriam-webster.com/dictionary/prophylactic.

Lam, "Nonatheromatous Arteriosclerosis", http://222.merckmanuals.com/profession/cardiovasculardisorders/arterioscl-erosis/non . . , accessed Dec. 29, 2015, 2 pages.

Lam, "Definition of Arteriosclerosis", http://www.merkmanuals.com/professional/cardiovascular-disorders/arterios-clerosis/defi . . , accessed Dec. 29, 2015, 1 page.

Lam, "Atherosclerosis", Atherosclerosis—Cardiovascular Disorders—Merck Manuals Professional Edition, http://www.merkmanuals.com/professional/cardiovascular-disorder/arteriosc-lerosis/atherosclerosis, accessed Dec. 29, 2015, 1-14.

Kerr et al., "(D-Ser2)Oxm[mPEG-PAL]: A novel modified analogue of oxyntomodulin with antihyperglycaemic, insullinotropic and anorexigenic actions", Biochemical Pharmacology, Dec. 2010, vol. 80, Issue 11, 1727-1735.

Hepatitis Health Center, "Fatty Liver Disease", http://www.webmd.com/hepatitis/fatty-liver-diseasepage=2&print=true, accessed Dec. 29, 2015, pp. 1-4.

Habegger et al, The metabolic actions of glucagon revisited, Nat. Rev. Endocrinol., 2010, 6, pp. 689-697.

Goldberg, "Dyslipidemia", Dyslipidemia—Endocrine and Metabolic Disorders—Merck Manuals Professional Edition, http://www.merckmanuals.com/professional/endocrine-and-metabolic-diorders- /lipid-dis . . , accessed Dec. 29, 2015, 11 pages.

Frankel et al., "Characterization of diphtheria fusion proteins targeted to the human interleukin-3 receptor", Protein Engineering, 2000, vol. 13, No. 8, pp. 575-581.

Eaton, Hypolipemic action of glucagon in experimental endogenous lipemia in the rat, Journal of Lipid Research, 1973, 14, pp. 312-318.

Drucker, "Glucagon-Like Peptides", Diabetes, Feb. 1998, vol. 47, 159-169.

Ding et al, Exendin-4, A Glucagon-Like Protein-1 (GLP-1) Receptor Agonist, Reverses Hepatic Steatosis in ob/ob Mice, Hepatology, 2006, 43, pp. 173-181.

Diabetes, from http://www.merckmanuals.com/professional/endocrine-and-metabolic-disorders/ . . . , pp. 1-34, accessed Sep. 2, 2016.

Dhanesha et al., "Treatment with exendin-4 improves the antidiabetic efficacy and reverses hepatic steatosis in glucokinase activator treated db/db mice", European Journal of Pharmacology, vol. 714, No. 1, Jun. 25, 2013, pp. 188-192.

Day et al, Optimization of Co-Agonism at GLP-1 and Glucagon Receptors to Safely Maximize Weight Reduction in DIO-Rodents, Peptide Science, 2012, 98, pp. 443-450, published online Apr. 14, 2012.

Day et al, A new glucagon and GLP-1 co-agonist eliminates obesity in rodents, Nature Chemical Biology, 2009, 5, pp. 749-757.

Collie et al, Purification and sequence of rat oxyntomodulin, Proc. Natl. Acad. Sci. USA, 1994, 91, pp. 9362-9366.

Clark et al., "Identifying and Managing Patients with Hyperlipidemia", The American Journal of Managed Care, Aug. 1997, vol. 3, No. 8, 1211-1219.

Chao-Lin et al., "Review on the effect of glucagon-like peptide-1 receptor agonists and dipeptidyl peptidase-4 inhibitors for the treatment of non-alcoholic fatty liver disease", Huashong University of Science and Technology Journal, vol. 35, No. 3, Jun. 1, 2015, pp. 333-336.

Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.

Berendsen, "A Glimpse of the Holy Grail?", Science, 1998, 282, 642-643.

"Prescription Medications for the Treatment of Obesity", U.S. Department of Health and Human Services, Apr. 1-8, 2013.

"Obesity", Merck Manual, http//:www.merckmanuals.com/professoinal/nutritional_disorders/obesity_and_the_metab., accessed Oct. 6, 2014, 1-9.

Watts et al., "Prediction of Glucose Response to Weight Loss in Patients With Non-Insulin-Dependent Diabetes Mellitus", Arch Intern Med, Apr. 1990, vol. 150, 803-806.

Olokoba et al., "Type 2 Diabetes Mellitus: A Review of Current Trends", Oman Medical Journal, 2012, vol. 27, No. 4, 269-273.

Franz et al., "The Dilemma of Weight Loss in Diabetes", Diabetes Spectrum, 2007, vol. 20, No. 3, 133-136.

* cited by examiner

COMPOSITION FOR TREATING DIABETES OR DIABESITY COMPRISING OXYNTOMODULIN ANALOG

CROSS-REFERENCE TO RELATED APPLICATIONS

This application is a divisional of U.S. application Ser. No. 14/440,653, filed May 5, 2015 (abandoned), which is the National Stage of International Application No. PCT/KR2013/009990, filed Nov. 6, 2013, which claims priority to Korean Patent Application No. 10-2012-0124724, filed Nov. 6, 2012. Each of the aforementioned applications is incorporated herein by reference in its entirety.

SEQUENCE LISTING

The instant application contains a Sequence Listing which has been submitted electronically in ASCII format and is hereby incorporated by reference in its entirety. The ASCII copy, created on Aug. 18, 2016, is named 106132_000119 SL.txt and is 40,393 bytes in size.

TECHNICAL FIELD

The present invention relates to a composition for preventing or treating diabetes, diabesity or diabetic complications, the composition comprising an oxyntomodulin analog as an active ingredient. Moreover, the present invention relates to a method for preventing or treating diabetes, diabesity or diabetic complications, the method comprising administering a pharmaceutically effective amount of an oxyntomodulin analog to a subject.

BACKGROUND

In recent years, in Korea, the intake of fats from foods has increased due to economic growth and the westernization of eating habits, and metabolic diseases such as hyperlipidemia, obesity, diabetes, hypertension, arteriosclerosis, and fatty liver disease, which are caused by a lack of exercise, have increased.

Diabetes is a kind of metabolic disease in which insulin secretion is insufficient or normal functions are not made (DeFronzo, 1988). Diabetes is characterized by increased blood glucose levels that cause various conditions and syndromes. In the case of diabetes, glucose is excreted with urine. In recent years, due to an increase in obesity, particularly abdominal obesity, the incidence of diabetes has explosively increased.

Worldwide, the number of diabetic patients was estimated to be 170 million in the year 2000 and expected to reach 370 million in the year 2030. However, a recent report showed that the number of diabetes already reached about 350 million worldwide in the year 2008 (Danaei et al., 2011), and thus it is much larger than expected. It was reported that about 80% or more of type 2 diabetic patients were obese, whereas only less than 10% of obese patients were diabetic (Harris et al., 1987). This relationship between diabetes and obesity is because fatty acids are accumulated in beta-cells or insulin-sensitive tissues such as the kidneys, the liver or the heart due to irregular secretion of adipokines and free fatty acids, resulting in lipotoxicity.

If a chronic hyperglycemic condition is not suitably treated, it leads to various pathological conditions in the body. Typically, it increases the risk of retinopathy, renal dysfunction, neuropathy, stroke caused by vascular disorder, kidney or heart diseases, diabetic foot ulcer, and cardiovascular disease. Such complications reduce the quality of life, and eventually reduce the life expectancy of diabetic patients. Thus, to prevent diabetic complications, the effective control of blood glucose levels is essential.

Current methods that are used to control blood glucose levels include lifestyle modification (diet therapy or exercise therapy) and drug therapy. However, diet therapy or exercise therapy is difficult to control and implement strictly, and the therapeutic effect thereof is also insufficient. Thus, most diabetic patients rely on lifestyle modification together with the control of blood glucose levels by drugs such as insulin, insulin secretion stimulators, insulin sensitivity enhancers, and blood glucose level lowering agents.

Insulin that is produced by recombination methods is an essential drug for type 1 diabetic patients and type 2 diabetic patients whose blood glucose levels are not controlled, and it is advantageous for controlling blood glucose levels. However, it has shortcomings, including a fearful feeling for hypodermic needles, difficulty in administration, risk of hypoglycaemia, and an increase in weight.

Meglitinides that are insulin secretion stimulators are drugs having a very quick effect, are taken before meals, and include NovoNorm (repaglinide), Fastic (nateglinide), Glufast (mitiglinide), etc. Insulin sensitivity enhancers are characterized in that they cause little or no hypoglycaemia when being taken alone, and examples thereof include metformin that is a biguanide drug, thiazolidinedione drugs such as Avandia (rosiglitazone), Actos (pioglitazone), etc.

Drugs that were recently developed include GLP-1 agonists developed based on the action of glucagon-like peptide-1, a hormone that stimulates insulin secretion, and examples of the GLP-1 agonists include exenatide and liraglutide. In addition, DPP-4 inhibitors are also recently developed new drugs, which inhibit the activity of DPP-4 (dipeptidyl peptidase-4), an enzyme that rapidly inactivates GLP-1, and typical examples thereof include Januvia (sitagliptin).

However, these drugs were reported to have side effects, including hepatotoxicity, gastrointestinal disorder, cardiovascular disease and carcinogenesis, and the annual cost for treatment of diabetes is also high, and thus is an obstacle in the treatment of diabetes. Indeed, the cost associated with pre-diabetes and diabetes reached about 200 trillion Won in the USA in the year 2007 (Dall et al., 2010), and the cost associated with obesity also reached 150 trillion Won in the USA in the year 2008 (Finkelstein et al., 2009).

Thus, there is an urgent need for the development of drugs, which can be used to treat both diabetes and diabesity by reducing weight and effectively lowering blood glucose levels and, at the same time, and have less side effects.

As a candidate for such drugs, oxyntomodulin has recently received attention. Oxyntomodulin is produced from pre-glucagon, a precursor, and is a peptide that can bind to both glucagon-like peptide-1 (GLP-1) and glucagon receptor to perform dual function. Because of such characteristics, oxyntomodulin has been studied for various purposes, including the treatment of obesity, diabetes, hyperlipidemia and fatty liver disease.

However, oxyntomodulin has a problem in that it should be administered at a high dose, because it has a short half-life in vivo and the activity thereof is insufficient for use in the treatment of obesity, diabetes, hyperlipidemia and fatty liver disease.

DISCLOSURE

Technical Problem

The present inventors have developed an oxyntomodulin analog having increased activity compared to native oxyntomodulin and have found that the oxyntomodulin analog reduces blood glucose levels, improve glucose tolerance and increases the ratio of glycated hemoglobin (HbA1c) in a high-fat diet-induced (HF DIO) mouse model and a diabetic mouse (db/db) model induced by a mutation in the leptin receptor, indicating that the oxyntomodulin analog can be effectively used for the treatment of diabetes, diabesity and diabetic complications, thereby completing the present invention.

Technical Solution

It is an object of the present invention to provide a composition for preventing or treating diabetes, diabesity and diabetic complications, comprising an oxyntomodulin analog as an active ingredient.

Another object of the present invention is to provide a method for preventing or treating diabetes, diabesity and diabetic complications, comprising administering a pharmaceutically effective amount of an oxyntomodulin analog to a subject.

Still another object of the present invention is to provide the use of the oxyntomodulin analog of the present invention in the preparation of a medicament for preventing or treating diabetes, diabesity and diabetic complications.

Advantageous Effects

The oxyntomodulin analog of the present invention has a high activity to activate GLP-1 receptor and glucagon receptor compared to native oxyntomodulin. Further, the oxyntomodulin analog of the present invention induces the expansion of beta-cells and increases insulin secretion, thereby reducing blood glucose levels that were increased by a high-calorie and high-fat diet. In addition, the oxyntomodulin analog induces decreases in body weight and diet intake to improve insulin sensitivity and allow blood glucose levels, which are not controlled due to insulin resistance, to be maintained at normal levels. Thus, the oxyntomodulin analog can be effectively used for the prevention or treatment of diabetes and related diseases.

BEST MODE

Figure 1:
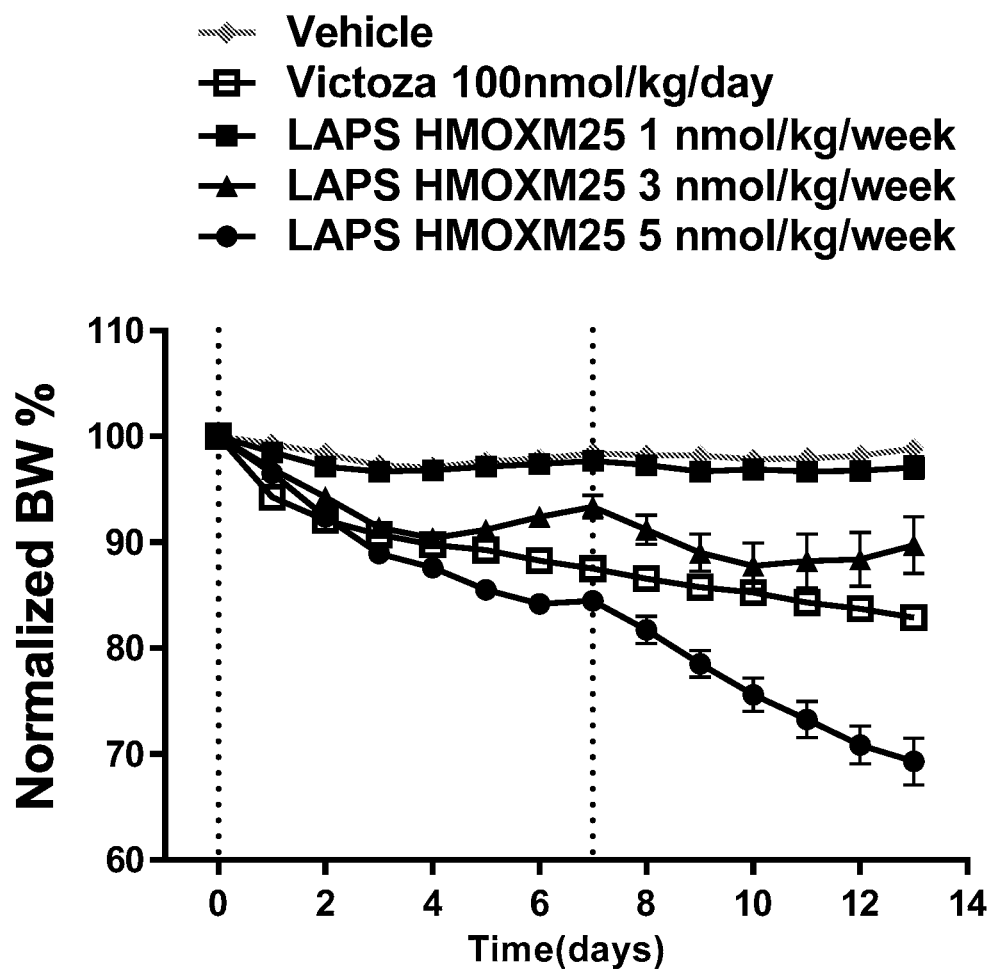
FIG. 1 is a graphic diagram showing the change in body weight caused by administration of a long-acting oxyntomodulin analog in mice with obesity induced by high-fat diet for a long period of time (26 weeks). The change in body weight was expressed as a percentage relative to the body weight measured at day 0.

In one aspect, the present invention provides a composition for preventing or treating diabetes, diabesity and diabetic complications, comprising an oxyntomodulin analog as an active ingredient.

As used herein, the term "oxyntomodulin" refers to a peptide produced from pre-glucagon that is a precursor of glucagon. In the present invention, oxyntomodulin is meant to include native oxyntomodulin and its precursor, analog, fragments and variants. Preferably, oxyntomodulin has an amino acid sequence of SEQ ID NO: 1 (HSQGTFTSDYSKYLDSRRAQDFVQWLMNTKRNRNNIA).

As used herein, the term "oxyntomodulin variant" is a peptide that has one or more amino acid residues different from those of the amino acid sequence of native oxyntomodulin and possesses a function of activating GLP-1 and glucagon receptors. The oxyntomodulin variant can be prepared by any one of substitution, addition, deletion, modification, or a combination thereof of some amino acids of native oxyntomodulin.

As used herein, the term "oxyntomodulin analog" refers to a peptide, peptide derivative or peptide mimic, which is prepared by the addition, deletion or substitution of some amino acids of native oxyntomodulin and can highly activate both GLP-1 receptor and glucagon receptor, compared to native oxyntomodulin.

As used herein, the term "oxyntomodulin fragment" refers to a fragment having an addition or deletion of one or more amino acids at the amino or carboxyl terminal end of native oxyntomodulin, in which the added amino acids may also be non-naturally occurring amino acids (e.g., D-type amino acid). This oxyntomodulin fragments has a function of regulating blood glucose levels in vivo.

Methods for preparing the oxyntomodulin variant, analog and fragment may be used alone or in combination. For example, the present invention includes a peptide, which has one or more amino acids different from those of native peptide, has deaminated amino acid residues at the N-terminus and has a function of activating both GLP-1 receptor and glucagon receptor.

Amino acids mentioned herein are abbreviated according to the nomenclature rules of IUPAC-IUB as follows:

| | |
|---|---|
| Alanine A; | Arginine R; |
| Asparagine N; | Aspartic acid D; |
| Cysteine C; | Glutamic acid E; |
| Glutamine Q; | Glycine G; |
| Histidine H; | Isoleucine I; |
| Leucine L; | Lysine K; |
| Methionine M; | Phenylalanine F |
| Proline P; | Serine S; |
| Threonine T; | Tryptophan W; |
| Tyrosine Y; | Valine V. |

In the present invention, the oxyntomodulin analog encompasses any peptide that is prepared by the substitution, addition, deletion or post-translational modification (e.g., methylation, acylation, ubiquitination, or intramolecular covalent bonding) of amino acids in the amino acid sequence of SEQ ID NO: 1 and can activate both the glucagon and GLP-1 receptors. Upon substitution or addition of amino acids, not only 20 amino acids commonly found in human proteins, but also atypical or non-naturally occurring amino acids can be used. Commercial sources of atypical amino acids include Sigma-Aldrich, ChemPep Inc., and Genzyme Pharmaceuticals. The peptides including these amino acids and atypical peptide sequences may be synthesized and purchased from commercial suppliers, for example, American Peptide Company or Bachem (USA) or Anygen (Korea).

In a specific embodiment of the present invention, the oxyntomodulin analog of the present invention is a novel peptide including the amino acid sequence of the following formula 1:

```
Formula 1
                                          (SEQ ID NO: 54)
R1-X1-X2-GTFTSD-X3-X4-X5-X6-X7-X8-X9-X10-X11-X12-
X13-X14-X15-X16-X17-X18-X19-X20-X21-X22-X23-X24-
R2
``` wherein

R1 is histidine, desamino-histidyl, dimethyl-histidyl (N-dimethyl-histidyl), beta-hydroxyimidazopropionyl, 4-imidazoacetyl, beta-carboxy imidazopropionyl or tyrosine;

X1 is Aib (aminosiobutyric acid), d-alanine, glycine, Sar (N-methylglycine), serine or d-serine;

X2 is glutamic acid or glutamine;

X3 is leucine or tyrosine;

X4 is serine or alanine;

X5 is lysine or arginine;

X6 is glutamine or tyrosine;

X7 is leucine or methionine;

X8 is aspartic acid or glutamic acid;

X9 is glutamic acid, serine or alpha-methyl-glutamic acid or is deleted;

X10 is glutamine, glutamic acid, lysine, arginine or serine or is deleted;

X11 is alanine, arginine or valine or is deleted;

X12 is alanine, arginine, serine or valine or is deleted;

X13 is lysine, glutamine, arginine or alpha-methyl-glutamic acid or is deleted;

X14 is aspartic acid, glutamic acid or leucine or is deleted;

X15 is phenylalanine or is deleted;

X16 is isoleucine or valine or is deleted;

X17 is alanine, cysteine, glutamic acid, lysine, glutamine or alpha-methyl-glutamic acid or is deleted;

X18 is tryptophan or is deleted;

X19 is alanine, isoleucine, leucine, serine or valine or is deleted;

X20 is alanine, lysine, methionine, glutamine or arginine or is deleted;

X21 is asparagine or is deleted;

X22 is alanine, glycine or threonine or is deleted;

X23 is cysteine or lysine or is deleted;

X24 is a peptide having 2 to 10 amino acids consisting of a combination of alanine, glycine and serine or is deleted; and R2 is KRNRNNIA (SEQ ID NO: 35), GPSSGAPPPS (SEQ ID NO: 36), GPSSGAPPPSK (SEQ ID NO: 37), HSQGTFTSDYSKYLD (SEQ ID NO: 38), HSQGTFTS-DYSRYLDK (SEQ ID NO: 39), HGEGTFTSDL-SKQMEEEAVK (SEQ ID NO: 40) or is deleted (with the exception of the case in which the amino acid sequence of formula 1 is identical to that of SEQ ID NO: 1).

In order to increase the activity of wild-type oxyntomodulin for the glucagon receptor and the GLP-1 receptor, the oxyntomodulin analog of the present invention may be substituted with 4-imidazoacetyl obtained by deletion of the alpha carbon of histidine at position 1 of the amino acid sequence of SEQ ID NO: 1, desamino-histidyl obtained by deletion of the N-terminal amino group, dimethyl-histidyl (N-dimethyl-histidyl) obtained by modification of the N-terminal amino group with two methyl groups, beta-hydroxy imidazopropionyl obtained by substitution of the N-terminal amino group with a hydroxyl group, or beta-carboxy imidazopropionyl obtained by substitution of the N-terminal amino group with a carboxyl group. In addition, the GLP-1 receptor-binding region may be substituted with amino acids that enhance hydrophobic and ionic bonds or a combination thereof. Further, a portion of the oxyntomodulin sequence may be substituted with the amino acid sequence of GLP-1 or Exendin-4 to increase the activity of the GLP-1 receptor.

Moreover, a portion of the oxyntomodulin sequence may be substituted with a sequence that enhances alpha helix. Preferably, amino acids at positions 10, 14, 16, 20, 24 and 28 of the amino acid sequence of formula 1 may be substituted with amino acids or amino acid derivatives consisting of Tyr(4-Me), Phe, Phe(4-Me), Phe(4-Cl), Phe(4-CN), Phe(4-NO$_2$), Phe(4-NH$_2$), Phg, Pal, Nal, Ala(2-thienyl) and Ala(benzothienyl) that are known to stabilize alpha helix, and the type and number of alpha helix-stabilizing amino acid or amino acid derivatives to be inserted are not limited. Preferably, amino acids at positions 10 and 14, 12 and 16, 16 and 20, 20 and 24, and 24 and 28 of the amino acid sequence may also be substituted with glutamic acid or lysine so as to form rings, and the number of rings to be inserted is not limited. Most preferably, the oxyntomodulin analog may have an amino acid sequence selected from among the following formulas 2 to 6.

In a specific embodiment, the oxyntomodulin analog of the present invention is a novel peptide including the amino acid sequence of the following formula 2, obtained by substitution of the amino acid sequence of oxyntomodulin with that of exendin or GLP-1:

R1-A-R3 (SEQ ID NO: 55)  Formula 2

In another specific embodiment, the oxyntomodulin analog of the present invention is a novel peptide including the amino acid sequence of the following formula 3, which is prepared by linking a portion of the amino acid sequence of oxyntomodulin and a portion of the amino acid sequence of exendin or GLP-1 via a proper amino acid linker:

R1-B-C-R4 (SEQ ID NO: 56)  Formula 3

In still another specific embodiment, the oxyntomodulin analog of the present invention is a novel peptide including the amino acid sequence of the following formula 4, wherein a portion of the amino acid sequence of oxyntomodulin is substituted with an amino acid that enhances the hydrophobic binding to GLP-1 receptor. For example, it is a peptide wherein Leu at position 26 is substituted with the amino acid Ile or Val that increases hydrophobicity.

```
Formula 4
                                          (SEQ ID NO: 57)
R1-SQGTFTSDYSKYLD-D1-D2-D3-D4-D5-LFVQW-D6-D7-N-D8-
R3
```

In still another specific embodiment, the oxyntomodulin analog of the present invention is a novel peptide including the amino acid sequence of the following formula 5, wherein a portion of the amino acid sequence of native oxyntomodulin is deleted, added, or substituted with other amino acids in order to increase the abilities of native oxyntomodulin to activate GLP-1 receptor and glucagon receptor:

Formula 5

(SEQ ID NO: 58)
R1-E1-QGTFTSDYSKYLD-E2-E3-RA-E4-E5-FV-E6-WLMNT-E7-R5

In formulas 2 to 5, R1 is as described in formula 1;
A is selected from the group consisting of

SQGTFTSDYSKYLDSRRAQDFVQWLMNT, (SEQ ID NO: 41)

SQGTFTSDYSKYLDEEAVRLFIEWLMNT, (SEQ ID NO: 42)

SQGTFTSDYSKYLDERRAQDFVAWLKNT, (SEQ ID NO: 43)

GQGTFTSDYSRYLEEEAVRLFIEWLKNG, (SEQ ID NO: 44)

GQGTFTSDYSRQMEEEAVRLFIEWLKNG, (SEQ ID NO: 45)

GEGTFTSDLSRQMEEEAVRLFIEWAA, (SEQ ID NO: 46)
and

SQGTFTSDYSRQMEEEAVRLFIEWLMNG; (SEQ ID NO: 47)

B is selected from the group consisting of

SQGTFTSDYSKYLDSRRAQDFVQWLMNT, (SEQ ID NO: 41)

SQGTFTSDYSKYLDEEAVRLFIEWLMNT, (SEQ ID NO: 42)

SQGTFTSDYSKYLDERRAQDFVAWLKNT, (SEQ ID NO: 43)

GQGTFTSDYSRYLEEEAVRLFIEWLKNG, (SEQ ID NO: 44)

GQGTFTSDYSRQMEEEAVRLFIEWLKNG, (SEQ ID NO: 45)

GEGTFTSDLSRQMEEEAVRLFIEWAA, (SEQ ID NO: 46)

SQGTFTSDYSRQMEEEAVRLFIEWLMNG, (SEQ ID NO: 47)

GEGTFTSDLSRQMEEEAVRLFIEW, (SEQ ID NO: 48)
and

SQGTFTSDYSRYLD; (SEQ ID NO: 49)

C is a peptide having 2 to 10 amino acids consisting of a combination of alanine, glycine and serine;
D1 is serine, glutamic acid or arginine;
D2 is arginine, glutamic acid or serine;
D3 is arginine, alanine or valine;
D4 is arginine, valine or serine;
D5 is glutamine, arginine or lysine;
D6 is isoleucine, valine or serine;
D7 is methionine, arginine or glutamine;
D8 is threonine, glycine or alanine;
E1 is serine, Aib, Sar, d-alanine or d-serine;
E2 is serine or glutamic acid;
E3 is arginine or lysine;
E4 is glutamine or lysine;
E5 is aspartic acid or glutamic acid;
E6 is glutamine, cysteine or lysine;
E7 is cysteine or lysine or is deleted;
R3 is KRNRNNIA (SEQ ID NO: 35), GPSSGAPPPS (SEQ ID NO: 36) or GPSSGAPPPSK (SEQ ID NO: 37);
R4 is HSQGTFTSDYSKYLD (SEQ ID NO: 38), HSQGTFTSDYSRYLDK (SEQ ID NO: 39) or HGEGTFTSDLSKQMEEEAVK (SEQ ID NO: 40); and
R5 is KRNRNNIA (SEQ ID NO: 35), GPSSGAPPPS (SEQ ID NO: 36) or GPSSGAPPPSK (SEQ ID NO: 37) or is deleted (with the exception of the case in which the amino acid sequences of formulas 2 to 5 are identical to that of SEQ ID NO: 1).

Preferably, the oxyntomodulin analog of the present invention may be a novel peptide of the following formula 6:

Formula 6

(SEQ ID NO: 59)
R1-X1-X2-GTFTSD-X3-X4-X5-X6-X7-X8-X9-X10-X11-X12-X13-X14-X15-X16-X17-X18-X19-X20-X21-X22-X23-X24-R2 wherein R1 is histidine, desamino-histidyl, 4-imidazoacetyl or tyrosine;
X1 is Aib(aminosiobutyric acid), glycine, serine or d-serine;
X2 is glutamic acid or glutamine;
X3 is leucine or tyrosine;
X4 is serine or alanine;
X5 is lysine or arginine;
X6 is glutamine or tyrosine;
X7 is leucine or methionine;
X8 is aspartic acid or glutamic acid;
X9 is glutamic acid or alpha-methyl-glutamic acid or is deleted;
X10 is glutamine, glutamic acid, lysine or arginine or is deleted;
X11 is alanine or arginine or is deleted;
X12 is alanine or valine or is deleted;
X13 is lysine, glutamine, arginine or alpha-methyl-glutamic acid or is deleted;
X14 is aspartic acid, glutamic acid or leucine or is deleted;
X15 is phenylalanine or is deleted;
X16 is isoleucine or valine or is deleted;
X17 is alanine, cysteine, glutamic acid, glutamine or alpha-methyl-glutamic acid or is deleted;
X18 is tryptophan or is deleted;
X19 is alanine, isoleucine, leucine or valine or is deleted;
X20 is alanine, lysine, methionine or arginine or is deleted;
X21 is asparagine or is deleted;
X22 is threonine or is deleted;
X23 is cysteine, lysine or is deleted;
X24 is a peptide having 2 to 10 amino acids consisting of glycine or is deleted; and
R2 is KRNRNNIA (SEQ ID NO: 35), GPSSGAPPPS (SEQ ID NO: 36), GPSSGAPPPSK (SEQ ID NO: 37), HSQGTFTSDYSKYLD (SEQ ID NO: 38), HSQGTFTSDYSRYLDK (SEQ ID NO: 39) or HGEGTFTSDLSKQMEEEAVK (SEQ ID NO: 40) or is deleted (with the exception of the case in which the amino acid sequence of formula 6 is identical to that of SEQ ID NO: 1).

More preferably, the oxyntomodulin analog of the present invention may be selected from the group consisting of the peptides of SEQ ID NOs: 2 to 34. Even more preferably, the oxyntomodulin analog of the present invention may be an oxyntomodulin analog described in Table 1 of Example 2-1.

In an example of the present invention, oxyntomodulin analogs having the amino acid sequences of SEQ ID NOs: 2 to 34, respectively, were prepared, and it was found that the oxyntomodulin analogs showed an excellent ability to activate GLP-1 receptor and glucagon receptor compared to native oxyntomodulin (Example 2). In other words, it could be seen from the above results that the oxyntomodulin analog of the present invention exhibited excellent effects on the prevention or treatment of diabetes, diabesity and/or diabetic complications compared to conventional oxyntomodulin by activating the GLP-1 receptor and the glucagon receptor.

The oxyntomodulin analogs of the present invention are present in the form of conjugates comprising various polymer in order to improve the therapeutic effect and in vivo half-life of the analogs.

The conjugates of the present invention have longer-acting effects than native oxyntomodulin, and the long-acting conjugates include an oxyntomodulin prepared by the modification, substitution, addition or deletion of the amino acids of native oxyntomodulin, an oxyntomodulin conjugated to a biodegradable polymer such as polyethylene glycol (PEG), an oxyntomodulin conjugated to a albumin, antibody, elastin, fibronectin or polysaccharide such as chitin or to a long-acting protein such as an immunoglobulin fragment, an oxyntomodulin conjugated to fatty acid having the ability of binding to albumin in vivo, or an oxyntomodulin encapsulated in biodegradable nanoparticles, and the type of long-acting conjugate that is used in the present invention is not limited.

Preferably, the conjugate is a conjugate wherein an oxyntomodulin analog having an amino acid sequence selected from the group consisting of the amino acid sequences of SEQ ID NOS: 2 to 34 is linked to an immunoglobulin Fc region through a non-peptidyl polymer.

The immunoglobulin Fc region is a biodegradable polypeptide that is metabolized in vivo, and thus is safe for use as a carrier for a drug. The immunoglobulin Fc region has a low molecular weight compared to the entire immunoglobulin molecule, and thus is advantageous in terms of the preparation, purification and yield of conjugates. In addition, because the amino acid sequence differs between antibodies, a Fab portion showing high non-homogeneity is removed, and thus the homogeneity of the material can be greatly increased and the possibility of inducing blood antigenicity can also be reduced.

As used herein, the term "immunoglobulin Fc region" refers to a protein that contains the heavy-chain constant region 2 (CH2) and heavy-chain constant region 3 (CH3) of an immunoglobulin, excluding the heavy-chain and light-chain variable regions, the heavy-chain constant region 1 (CH1) and the light-chain constant region 1 (CL1) of the immunoglobulin. It may further include a hinge region at the heavy-chain constant region. Also, the immunoglobulin Fc region of the present invention may be an expanded Fc region including part or all of the heavy-chain constant region 1 (CH1) and/or the light-chain constant region 1 (CL1), except for the heavy-chain and light-chain variable regions, as long as it has an effect that is substantially equal to or better than the native protein. Further, the immunoglobulin Fc region may be a region having a deletion of a portion of a relatively long amino acid sequence corresponding to CH2 and/or CH3. Specifically, the immunoglobulin Fc region of the present invention may comprise 1) a CH1 domain, a CH2 domain, a CH3 domain and a CH4 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), or 6) a dimer of each domain of the heavy-chain constant regions and the light-chain constant region.

The immunoglobulin Fc region of the present invention includes a native amino acid sequence, and a sequence derivative (mutant) thereof. As used herein, the term "amino acid sequence derivative" refers to a sequence that is different from the native amino acid sequence due to the deletion, insertion, non-conservative or conservative substitution or a combination thereof of one or more amino acid residues of the native amino acid sequence. For example, in the case of an IgG Fc, amino acid residues at positions 214 to 238, 297 to 299, 318 to 322, or 327 to 331, which are known to be important in binding, may be used as suitable sites for modification.

In addition, other various derivatives are possible, including one that has a deletion of a region capable of forming a disulfide bond, or a deletion of some amino acid residues at the N-terminal end of native Fc or an addition of a methionine residue at the N-terminal end of native Fc. Further, to remove effector functions, a deletion may occur in a complement-binding site, such as a C1q-binding site and an ADCC (antibody dependent cell mediated cytotoxicity) site. Techniques of preparing such sequence derivatives of the immunoglobulin Fc region are disclosed in International Patent Publication Nos. WO 97/34631, WO 96/32478, etc.

Amino acid exchanges in proteins and peptides, which do not generally alter the activity of the proteins or peptides, are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in both directions. In addition, the Fc region may, if necessary, be modified by phosphorylation, sulfation, acrylation, glycosylation, methylation, farnesylation, acetylation, amidation, and the like.

The above-described Fc derivatives show biological activity identical to that of the Fc region of the present invention or have increased structural stability against heat, pH, or the like.

In addition, this Fc region may be obtained from native forms isolated from humans and other animals including cows, goats, pigs, mice, rabbits, hamsters, rats and guinea pigs, or may be recombinants or derivatives thereof, obtained from transformed animal cells or microorganisms. Herein, the Fc region may be obtained from a native immunoglobulin by isolating a whole immunoglobulin from a living human or animal body and treating the isolated immunoglobulin with proteinase. When the whole immunoglobulin is treated with papain, it is cleaved into Fab and Fc regions, and when the whole immunoglobulin is treated with pepsin, it is cleaved into pF'c and F(ab)$_2$ fragments. Fc or pF'c can be isolated using size exclusion chromatography or the like. Preferably, a human-derived Fc region is a recombinant immunoglobulin Fc region obtained from a microorganism.

In addition, the immunoglobulin Fc region may be in the form of having native sugar chains or increased or decreased sugar chains compared to a native form, or may be in a deglycosylated form. The increase, decrease or removal of the immunoglobulin Fc sugar chains may be achieved by conventional methods such as a chemical method, an enzymatic method and a genetic engineering method using a microorganism. The Fc region obtained by removal of sugar chains from Fc shows a significant decrease in binding affinity to the C1q part and a decrease or loss in antibody-dependent cell-mediated cytotoxicity or complement-dependent cytotoxicity, and thus does not induce unnecessary immune responses in vivo. In this regard, an immunoglobulin Fc region in a deglycosylated or aglycosylated form may be more suitable to the object of the present invention as a drug carrier.

As used herein, the term "deglycosylation" refers to enzymatically removing sugar moieties from an Fc region, and the term "aglycosylation" refers to an unglycosylated Fc region produced in a prokaryote, preferably E. coli.

Meanwhile, the immunoglobulin Fc region may be derived from humans or other animals including cows, goats, pigs, mice, rabbits, hamsters, rats and guinea pigs. Preferably, it is derived from humans.

In addition, the immunoglobulin Fc region may be derived from IgG, IgA, IgD, IgE, IgM, or a combination or hybrid thereof. Preferably, it is derived from IgG or IgM, which are among the most abundant proteins in human blood, and most preferably from IgG known to enhance the half-lives of ligand-binding proteins.

As used herein, the term "combination" means that polypeptides encoding single-chain immunoglobulin Fc regions of the same origin are linked to a single-chain polypeptide of a different origin to form a dimer or multimer. Specifically, a dimer or multimer may be formed from two or more fragments selected from the group consisting of IgG Fc, IgA Fc, IgM Fc, IgD Fc, and IgE Fc fragments.

As used herein, the term "hybrid" means that sequences corresponding to two or more immunoglobulin Fc fragments of different origins are present in a single-chain immunoglobulin Fc region. In the present invention, various forms of hybrid are possible. In other words, a hybrid composed of 1 to 4 domains selected from the group consisting of the CH1, CH2, CH3 and CH4 of IgG Fc, IgM Fc, IgA Fc, IgE Fc and IgD Fc is possible, and it may include a hinge.

Meanwhile, IgG can also be sub-classified into IgG1, IgG2, IgG3 and IgG4, and in the present invention, a combination or hybrid of these subclasses is also possible. Preferably, IgG is the IgG2 ad IgG4 subclass, and most preferably, it is the Fc region of IgG4 that substantially lacks effector functions such as complement-dependent cytotoxicity (CDC).

In other words, the most preferred immunoglobulin Fc region that is used as a drug carrier in the present invention is an Fc region derived from human IgG4. A human-derived Fc region is more preferable than a non-human-derived Fc region, which may act as an antigen in the human body and cause undesirable immune responses such as the production of a new antibody against the antigen.

As used herein, the term "non-peptidyl polymer" refers to a biocompatible polymer including two or more repeating units linked to each other by any covalent bond in place of a peptide bond. In the present invention, the non-peptidyl polymer may be used interchangeably with the non-peptidyl linker.

The non-peptidyl polymer that can be used in the present invention may be selected from the group consisting of polyethylene glycol, polypropylene glycol, an ethylene glycol/propylene glycol copolymer, polyoxyethylated polyol, polyvinyl alcohol, polysaccharides, dextran, polyvinyl ethyl ether, biodegradable polymers such as PLA (poly(lactic acid)) and PLGA (polylactic-glycolic acid), lipid polymers, chitins, hyaluronic acid, and combinations thereof. Preferably, the non-peptidyl polymer is polyethylene glycol. In addition, derivatives thereof known in the art and derivatives that may be easily prepared by a method known in the art also fall within the scope of the present invention.

The peptide linker that is used in a fusion protein obtained by a conventional inframe fusion method has drawbacks in that it is easily cleaved by proteinase in vivo, and thus a sufficient effect of increasing the serum half-life of the active drug by a carrier cannot be obtained as expected. However, in the present invention, the polymer having resistance to proteinase can be used to maintain the serum half-life of the peptide, similar to the carrier. Therefore, any non-peptidyl polymer can be used without limitation in the present invention, as long as it is a polymer having the aforementioned function, that is, a polymer having resistance to proteinase in vivo. The non-peptidyl polymer has a molecular weight in the range of 1 to 100 kDa, and preferably 1 to 20 kDa. The non-peptidyl polymer of the present invention, which is linked to the immunoglobulin Fc region, may be one kind of polymer or a combination of different polymers.

The non-peptidyl polymer that is used in the present invention may have a reactive group capable of binding to the immunoglobulin Fc region and the protein drug. The reactive group at both ends of the non-peptidyl polymer is preferably selected from the group consisting of a reactive aldehyde group, a propionaldehyde group, a butyraldehyde group, a maleimide group and a succinimide derivative.

The succinimide derivative may be succinimidyl propionate, hydroxy succinimidyl, succinimidyl carboxymethyl, or succinimidyl carbonate. In particular, when the non-peptidyl polymer has a reactive aldehyde group at both ends thereof, non-specific reactions can be minimized, and a physiologically active polypeptide and an immunoglobulin can be effectively bound to both ends of the non-peptidyl polymer, respectively. A final product generated by reductive alkylation with an aldehyde bond is much more stable than that linked by an amide bond. The aldehyde reactive group selectively binds to an N-terminus at a low pH and can form a covalent bond with a lysine residue at a high pH such as pH 9.0.

The reactive groups at both ends of the linker that is the non-peptidyl polymer may be the same or different. For example, the non-peptidyl polymer may possess a maleimide group at one end, and an aldehyde group, a propionaldehyde group or a butyraldehyde group at the other end. When a polyethylene glycol having a reactive hydroxy group at both ends thereof is used as the non-peptidyl polymer, the hydroxy group may be activated to various reactive groups by known chemical reactions, or a polyethylene glycol having a commercially available modified reactive group may be used so as to prepare the long-acting conjugate of the present invention.

The conjugate of the present invention may be one in which each end of the non-peptidyl polymer is linked to the immunoglobulin Fc region and the amine or thiol group of the oxyntomodulin analog, respectively.

Meanwhile, in the present invention, both ends of the non-peptidyl polymer include reactive groups to which an immunoglobulin Fc region and a protein drug can bind. Examples of the reactive groups include, but are not limited to, an aldehyde group, a propionaldehyde group or a butyraldehyde group, a maleimide group, a succinimide derivative (succinimidyl propionate, hydroxyl succinimidyl, succinimidyl propionate carboxymethyl or succinimidyl carbonate) and the like.

The reactive groups at both ends of the linker that is the non-peptidyl polymer may be the same or different. For example, the non-peptidyl polymer may have a maleimide group at one end and an aldehyde group, a propionaldehyde group or a butyraldehyde group at the other end. For example, when the non-peptidyl polymer has a reactive aldehyde group at one end and a reactive maleimide group at the other end, non-specific reactions can be minimized, and a physiologically active polypeptide and an immunoglobulin can be effectively bound to both ends of the non-peptidyl polymer. In an example of the present invention, a conjugate was synthesized by linking oxyntomodulin or its analog to the immunoglobulin Fc region via a covalent bond using the non-peptidyl polymer PEG including a propionaldehyde group alone or both a maleimide group and an aldehyde group.

The pharmaceutical composition of the present invention can be used for the prevention or treatment of diabetes, diabesity and/or diabetic complications.

As used herein, the term "prevention" refers to all actions that inhibit or delay the development of a target disease. Specifically, the term "prevention" means administering the oxyntomodulin analog of the present invention to control blood glucose levels to normal levels to thereby inhibit or delay the development of diabetes, diabesity or diabetic complications.

As used herein, the term "treatment" refers to all actions that alleviate, ameliorate or relieve the symptoms of the disease developed. Specifically, the term "treatment" means administering the oxyntomodulin analog of the present invention to maintain blood glucose levels stably at normal levels to thereby alleviate, ameliorate or relieve the conditions of diabetes, diabesity or diabetic complications.

As used herein the term "diabetes" is a kind of metabolic disease in which insulin secretion is insufficient or normal functions are not made. Diabetes is characterized by increased blood glucose levels that cause various conditions and syndromes. In the case of diabetes, glucose is excreted with urine.

As used herein, the term "diabesity" refers to diabetes accompanied by obesity conditions, particularly type 2 diabetes, or obesity conditions that generally appear in type 2 diabetic patients. About 80-90% of type 2 diabetic patients have obesity conditions and are characterized by insulin resistances. Proper exercise, diet therapy and drug therapy can prevent diabesity and alleviate the conditions of diabesity. In the present invention, diabsety may mean one resulting from obesity.

As used herein, the term "diabetic complications" refers to various pathological conditions occurring in the body due to hyperglycemic conditions maintained for a long period of time. Examples of diabetic complications include, but are not limited to, retinopathy, renal dysfunction, neuropathy, stroke caused by vascular disorder, kidney or heart diseases, diabetic foot ulcer, and cardiovascular disease. If a hyperglycemic condition is maintained for a long period of time, it leads to various pathological conditions in the body. Typically, it increases the risk of retinopathy, renal dysfunction, neuropathy, stroke caused by vascular disorder, kidney or heart diseases, diabetic foot ulcer, and cardiovascular disease. Thus, to prevent diabetic complications, the effective control of blood glucose levels is essential.

Accordingly, the pharmaceutical composition of the present invention can be used for the prevention or treatment of diabetes, diabesity or diabetic complications.

In an example of the present invention, a long-acting oxyntomodulin analog conjugate of the present invention was prepared by covalently linking the oxyntomodulin analog of the present invention to an immunoglobulin Fc region by polyethylene glycol, and the prepared conjugate was administered to a mouse model with obesity induced by high-fat diet and a mouse model with diabetes induced by a mutation in the leptin receptor. As a result, it was shown that the body weight and feed intake of the group administered with the long-acting oxyntomodulin analog conjugate of the present invention significantly decreased those of the obesity-induced animal model (FIG. 1) and that the blood glucose level significantly decreased (FIG. 2). In addition, the long-acting oxyntomodulin analog conjugate of the present invention showed a blood glucose lowering effect equal to or higher than VICTOZA a commercially available long-acting GLP-1 analog (FIG. 2).

In an example of the present invention, a long-acting oxyntomodulin analog conjugate was prepared by covalently linking the oxyntomodulin analog of the present invention to an immunoglobulin Fc region, and the prepared conjugate was administered to a mouse model with diabetes induced by a mutation in the leptin receptor. As a result, it was shown that, in the group administered with the long-acting oxyntomodulin analog conjugate, an increase in the body weight was significantly inhibited compared to that of the control group (FIG. 3), and the blood glucose level significantly decreased (FIG. 4), and also the conjugate showed a superior blood glucose lowering effect compared to VICTOZA a commercially available long-acting GLP-1 analog (FIG. 4).

In other words, the oxyntomodulin analog according to the present invention functions to induce the expansion of beta-cells in vivo to increase insulin secretion, thereby improving the ability to control blood glucose levels. In addition, the oxyntomodulin analog according to the present invention induces a decrease in body weight to improve insulin sensitivity and prevent the development of cardiovascular diseases, including arteriosclerosis, hyperlipidemia and hypertension, which can be developed die to insulin resistance. Accordingly, the oxyntomodulin analog of the present invention can be effectively used as an agent for treating diabetes, diabesity and diabetic complications. Additionally, the conjugate of the present invention has a high ability to activate the GLP-1 receptor and the glucagon receptor, compared to native oxyntomodulin, and it shows an increased blood half-life in vivo due to the Fc region bound thereto, and thus the activity thereof can be maintained in vivo for an extended period of time.

The composition of the present invention may be a pharmaceutical composition.

The pharmaceutical composition of the present invention may further comprise a pharmaceutical agent showing a preventive or therapeutic effect against diabetes, diabesity or diabetic complications. In order to administer the oxyntomodulin analog of the present invention in combination with a pharmaceutical agent known as a therapeutic agent against diabetes, diabesity or diabetic complications, the composition of the present invention may further comprise this known pharmaceutical agent.

Thus, the composition of the present invention may be used alone or administered in combination with other drugs in order to prevent or treat diabetes, diabesity or diabetic complications.

As used herein, the term "administration" means introducing a given material into a patient by any appropriate method. The analog of the present invention may be administered by any general route, as long as it can reach a target tissue. Specifically, the analog of the present invention may be administered intraperitoneally, intravenously, intramuscularly, subcutaneously, intradermally, orally, locally, intranasally, intrapulmonarily or intrarectally, but is not limited thereto. However, because the peptide is digested when being administered orally, the oral composition is preferably formulated so that the active ingredient is coated or protected from degradation in the stomach. Preferably, the composition of the present invention may be administered in an injectable form. In addition, the pharmaceutical composition of the present invention may be administered using any system capable of delivering the active ingredient to target cells.

The pharmaceutical composition comprising the oxyntomodulin analog of the present invention may further comprise a pharmaceutically acceptable carrier. For oral administration, pharmaceutically acceptable carriers include a binder, a lubricant, a disintegrant, an excipient, a solubilizer, a dispersing agent, a stabilizer, a suspending agent, a colorant, and a flavoring agent. For injectable preparations, pharmaceutically acceptable carriers include a buffer, a preservative, an analgesic, a solubilizer, an isotonic agent, and a stabilizer. For topical administration, pharmaceutically acceptable carriers include a base, an excipient, a lubricant, and a preservative. The pharmaceutical composition of the present invention may be formulated in various dosage forms using the aforementioned pharmaceutically acceptable carriers. For example, for oral administration, the pharmaceutical composition may be formulated into tablets, troches, capsules, elixirs, suspensions, syrups, wafers or the like. For injectable preparations, the pharmaceutical composition may be provided in the form of a unit dosage ampoule or a multiple dosage container. In addition, the pharmaceutical composition may also be formulated into solutions, suspensions, tablets, pills, capsules and sustained-release preparations.

Meanwhile, examples of the carrier, excipient and diluent suitable for formulation include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical composition of the present invention may further include fillers, anti-coagulating agents, lubricants, wetting agents, flavors, preservative and the like.

The dose of the pharmaceutical composition of the present invention is determined according to the kind of active ingredient together with various factors such as the disease to be treated, the route of administration, the patient's age, sex and weight, and the severity of the disease. The pharmaceutical composition of the present invention has a long in vivo half-life and excellent bioavailability, and thus the number and frequency of administration of the pharmaceutical composition can be significantly reduced.

In another aspect, the present invention provides a method for preventing or treating diabetes, diabesity or diabetic complications, the method comprising administering a pharmaceutically effective amount of the oxyntomodulin analog to a subject.

Herein, the oxyntomodulin analog, diabetes, diabesity and diabetic complications are as defined above.

As used herein, the term "subject" refers to a subject suspected of having diabetes, diabesity or diabetic complications. Specifically, the term means mammals, including humans, rats and domestic animals, which have or are at the risk of developing the above disease. In addition, the subject may be any subject that can be treated by the oxyntomodulin analog of the present invention.

The therapeutic method of the present invention may comprise administering a pharmaceutically effective amount of the pharmaceutical composition comprising the conjugate. The total daily dose of the composition can be determined through appropriate medical judgment by a physician, and the composition may be administered once or several times. However, in view of the purpose of the present invention, the specific therapeutically effective dose of the composition for any particular patient may vary depending on various factors well known in the medical field, including the kind and degree of response to be achieved, concrete compositions according to whether other agents are used therewith or not, the patient◎ age, body weight, health condition, sex and diet, the time and route of administration, the secretion rate of the composition, the duration of treatment, other drugs used in combination or coincident with the composition of the present invention, and other factors known in the medical field.

In still another aspect, the present invention provides the use of the oxyntomodulin analog of the present invention in the preparation of a medicament for preventing or treating diabetes, diabesity or diabetic complications.

In yet another aspect, the present invention provides a method for preparing the oxyntomodulin analog conjugate.

The preparation method of the present invention may comprise the steps of: (1) covalently linking a non-peptidyl polymer having a reactive aldehyde, maleimide or succinimide group at both ends to the amine or thiol group of an oxyntomodulin analog peptide; (2) separating a conjugate comprising the oxyntomodulin analog peptide, having the non-peptidyl polymer covalently linked thereto at positions other than the amino terminal end, from the reaction mixture of step (1); and (3) covalently linking an immunoglobulin Fc region to the other end of the linked non-peptidyl polymer of the separated conjugate, thereby producing a peptide conjugate comprising the immunoglobulin Fc region and the oxyntomodulin analog peptide, linked to both ends of the non-peptidyl polymer, respectively.

More specifically, the preparation method may comprise the steps of: (1) covalently linking a non-peptidyl polymer, having a reactive aldehyde group and a reactive maleimide group at each end thereof, to the cysteine residue of an oxyntomodulin analog; (2) separating a conjugate comprising the oxyntomodulin analog, having the non-peptidyl polymer covalently linked to the cysteine residue, from the reaction mixture of step (1); and (3) covalently linking an immunoglobulin Fc region to the other end of the linked non-peptidyl polymer of the separated conjugate, thereby producing a peptide conjugate comprising the immunoglobulin Fc region and the oxyntomodulin analog, linked to both ends of the non-peptidyl polymer, respectively.

MODE FOR INVENTION

Hereinafter, the present invention will be described in further detail with reference to examples. It is to be understood, however, that these examples are for illustrative purposes only and are not intended to limit the scope of the present invention.

Example 1: Production of Cell Line for In Vitro Activation

Example 1-1: Production of Cell Line Showing cAMP Response to GLP-1

Using a portion corresponding to the ORF (open reading frame) of cDNA (OriGene Technologies, Inc. USA) of the human GLP-1 receptor gene as a template, PCR was performed using reverse and forward primers including a HindIII cleavage site and an EcoRI cleavage site, respectively, thereby obtaining a PCR product.

Forward primer:
(SEQ ID NO: 50)
5'-CCCGGCCCCCGCGGCCGCTATTCGAAATAC-3'

Reverse primer:
SEQ ID NO: 51)
5'-GAACGGTCCGGAGGACGTCGACTCTTAAGATAG-3'

The PCR product was cloned into the known animal cell expression vector x0GC/dhfr, thereby constructing the recombinant vector x0GC/GLP-1R.

The recombinant vector x0GC/GLP-1R was introduced into a CHO DG44 cell line, cultured in DMEM/F12 (10% FBS) medium, using lipofectamine (Invitrogene, USA), to obtain a transformant. The transformant was incubated in a selective medium containing 1 mg/mL G418 and 10 nM methotraxate, and monoclonal cell lines were selected therefrom. Then, a cell line showing a good concentration-dependent cAMP response to GLP-1 was finally selected from the monoclonal cell lines.

Example 1-2: Production of Cell Line Showing cAMP Response to Glucagon

Using a portion corresponding to the ORF (open reading frame) of cDNA (OriGene Technologies, Inc. USA) of the human glucagon receptor gene as a template, PCR was performed using reverse and forward primers including an EcoRI cleavage site and a XhoI cleavage site, respectively, thereby obtaining a PCR product.

Forward primer:
(SEQ ID NO: 52)
5'-CAGCGACACCGACCGTCCCCCCGTACTTAAGGCC-3'

Reverse Primer:
(SEQ ID NO: 53)
5'-CTAACCGACTCTCGGGGAAGACTGAGCTCGCC-3'

The PCR product was cloned into the known animal cell expression vector x0GC/dhfr, thereby constructing the recombinant vector x0GC/GCGR.

The recombinant vector x0GC/GCGR was introduced into a CHO DG44 cell line, cultured in DMEM/F12 (10% FBS) medium, using lipofectamine (Invitrogene, USA), to obtain a transformant. The transformant was incubated in a selective medium containing 1 mg/mL G418 and 10 nM methotraxate, and monoclonal cell lines were selected therefrom. Then, a cell line showing a good concentration-dependent cAMP response to glucagon was finally selected from the monoclonal cell lines.

Example 2: In Vitro Activity of Oxyntomodulin Analogs

Example 2-1: Synthesis of Oxyntomodulin Analogs

In order to measure the in vitro activities of oxyntomodulin analogs, oxyntomodulin analogs having the amino acid sequences shown in Table 1 below were synthesized.

TABLE 1

| Oxyntomodulin and oxyntomodulin analogs | |
|---|---|
| SEQ ID NO | Sequence |
| SEQ ID NO: 1 | HSQGTFTSDYSKYLDSRRAQDFVQWLMNTKRNRNNIA |
| SEQ ID NO: 2 | CA-SQGTFTSDYSKYLDEEAVRLFIEWLMNTKRNRNNIA |
| SEQ ID NO: 3 | CA-SQGTFTSDYSKYLDERRAQDFVAWLKNTGPSSGAPPPS |
| SEQ ID NO: 4 | CA-GQGTFTSDYSRYLEEEAVRLFIEWLKNGGPSSGAPPPS |
| SEQ ID NO: 5 | CA-GQGTFTSDYSRQMEEEAVRLFIEWLKNGGPSSGAPPPS |
| SEQ ID NO: 6 | CA-GEGTFTSDLSRQMEEEAVRLFIEWAAHSQGTFTSDYSKYLD |
| SEQ ID NO: 7 | CA-SQGTFTSDYSRYLDEEAVRLFIEWLMNTK |
| SEQ ID NO: 8 | CA-SQGTFTSDLSRQLEEEAVRLFIEWLMNK |
| SEQ ID NO: 9 | CA-GQGTFTSDYSRYLDEEAVXLFIEWLMNTKRNRNNIA |
| SEQ ID NO: 10 | CA-SQGTFTSDYSRQMEEEAVRLFIEWLMNGGPSSGAPPPSK |
| SEQ ID NO: 11 | CA-GEGTFTSDLSRQMEEEAVRLFIEWAAHSQGTFTSDYSRYLDK |
| SEQ ID NO: 12 | CA-SQGTFTSDYSRYLDGGGHGEGTFTSDLSKQMEEEAVK |
| SEQ ID NO: 13 | CA-SQGTFTSDYSRYLDXEAVXLFIEWLMNTK |
| SEQ ID NO: 14 | CA-GQGTFTSDYSRYLDEEAVXLFIXWLMNTKRNRNNIA |
| SEQ ID NO: 15 | CA-GQGTFTSDYSRYLDEEAVRLFIXWLMNTKRNRNNIA |
| SEQ ID NO: 16 | CA-SQGTFTSDLSRQLEGGGHSQGTFTSDLSRQLEK |
| SEQ ID NO: 17 | CA-SQGTFTSDYSRYLDEEAVRLFIEWIRNTKRNRNNIA |
| SEQ ID NO: 18 | CA-SQGTFTSDYSRYLDEEAVRLFIEWIRNGGPSSGAPPPSK |

TABLE 1-continued

Oxyntomodulin and oxyntomodulin analogs

| SEQ ID NO | Sequence |
|---|---|
| SEQ ID NO: 19 | CA-SQGTFTSDYSRYLDEEAVXLFIEWIRNTKRNRNNIA |
| SEQ ID NO: 20 | CA-SQGTFTSDYSRYLDEEAVXLFIEWIRNGGPSSGAPPPSK |
| SEQ ID NO: 21 | CA-SQGTFTSDYSRQLEEEAVRLFIEWVRNTKRNRNNIA |
| SEQ ID NO: 22 | DA-SQGTFTSDYSKYLDEKRAKEFVQWLMNTK |
| SEQ ID NO: 23 | HAibQGTFTSDYSKYLDEKRAKEFVCWLMNT |
| SEQ ID NO: 24 | HAibQGTFTSDYSKYLDEKRAKEFVQWLMNTC |
| SEQ ID NO: 25 | HAibQGTFTSDYSKYLDEKRAKEFVQWLMNTC |
| SEQ ID NO: 26 | HAibQGTFTSDYSKYLDEKRAKEFVQWLMNTC |
| SEQ ID NO: 27 | HAibQGTFTSDYSKYLDEQAAKEFICWLMNT |
| SEQ ID NO: 28 | HAibQGTFTSDYSKYLDEKRAKEFVQWLMNT |
| SEQ ID NO: 29 | H(d)SQGTFTSDYSKYLDSRRAQDFVQWLMNTKRNRNNIA |
| SEQ ID NO: 30 | CA-SQGTFTSDYSKYLDSRRAQDFVQWLMNTKRNRNNIA |
| SEQ ID NO: 31 | CA-(d)SQGTFTSDYSKYLDSRRAQDFVQWLMNTKRNRNNIA |
| SEQ ID NO: 32 | CA-AibQGTFTSDYSKYLDEKRAKEFVQWLMNTC |
| SEQ ID NO: 33 | HAibQGTFTSDYAKYLDEKRAKEFVQWLMNTC |
| SEQ ID NO: 34 | YAibQGTFTSDYSKYLDEKRAKEFVQWLMNTC |

In Table 1 above, the amino acids indicated by the bold letters mean ring formation, and the amino acids indicated by X mean alpha-methyl-glutamic acids that are non-native amino acids. In addition, CA indicates 4-imidazoacetyl, DA indicates desamino-histidyl, and (d)S indicates d-serine.

Example 2-2: Measurement of In Vitro Activities of Oxyntomodulin Analogs

In order to measure the effects of the peptides prepared in Example 2-1 above, the in vitro activities of the peptides in cells were measured using the transformants prepared in Examples 1-1 and 1-2.

Each of the transformants was transformed so as to express each of human GLP-1 receptor and glucagon receptor genes in CHO (Chinese hamster ovary) and was suitable for measuring the activities of GLP-1 and glucagon. Thus, the activity of each of the oxyntomodulin analogs was measured using each of the transformants.

Specifically, each of the transformants was subcultured twice or three times a week, and the cells were dispensed into each well of a 96-well plate at a density of $1 \times 10^5$ cells/well and cultured for 24 hours.

The cultured cells were washed with KRB buffer, suspended in 40 ml of 1 mM IBMX-containing KRB buffer, and then allowed to stand at room temperature for 5 minutes. Each of oxyntomodulin (SEQ ID NO: 1) and the oxyntomodulin analogs (SEQ ID NOS: 2-6, 8, 10-13, 17, 18, 23-25, 27, 28 and 32-34) was serially diluted by five-fold from 1000 nM to 0.02 nM, and 40 Ml of each of the dilutions was added to the cells, which were then incubated in a $CO_2$ incubator at 37° C. for 1 hour. Then, 20 ml of cell lysis buffer was added to lyse the cells, and the concentration of cAMP in each of the cell lysates was measured using a cAMP assay kit (Molecular Device, USA). From the results of the measurement, $EC_{50}$ values were calculated and compared with each other (Table 2).

Comparison of in vitro activities of GLP-1 receptor and glucagon receptor between oxyntomodulin analogs

TABLE 2

| | $EC_{50}$ (nM) | |
|---|---|---|
| SEQ ID NO | CHO/GLP-1R | CHO/GCGR |
| SEQ ID NO: 1 | 50-210 | 10-43 |
| SEQ ID NO: 2 | 51.8 | 12.8 |
| SEQ ID NO: 3 | >1,000 | 637.7 |
| SEQ ID NO: 4 | 5.5 | >1,000 |
| SEQ ID NO: 5 | 5.9 | >1,000 |
| SEQ ID NO: 6 | 500.1 | >1,000 |
| SEQ ID NO: 8 | 419.6 | >1,000 |
| SEQ ID NO: 10 | >1,000 | >1,000 |
| SEQ ID NO: 11 | >1,000 | >1,000 |
| SEQ ID NO: 12 | >1,000 | >1,000 |
| SEQ ID NO: 13 | >1,000 | >1,000 |
| SEQ ID NO: 17 | 97.9 | >1,000 |
| SEQ ID NO: 18 | 96.3 | >1,000 |
| SEQ ID NO: 23 | 2.46 | 5.8 |
| SEQ ID NO: 24 | 1.43 | 6.95 |
| SEQ ID NO: 25 | 1.9 | 1.3 |
| SEQ ID NO: 27 | 2.8-5.5 | 3.1-5.6 |
| SEQ ID NO: 28 | 3.1 | 0.3 |
| SEQ ID NO: 32 | 41.3 | 17.7 |
| SEQ ID NO: 33 | 2.2 | 80.2 |
| SEQ ID NO: 34 | 12.5 | 1.04 |

As can be seen in Table 2 above, the oxyntomodulin analogs showed excellent in vitro GLP-1 and glucagon receptor activities compared to the oxyntomodulin of SEQ ID NO: 1.

Oxyntomodulin is known to have the effect of treating obesity, hyperlipidemia, fatty liver disease or arteriosclerosis by activating the GLP-1 receptor and the glucagon receptor. The oxyntomodulin analogs according to the present invention have a high ability to activate the GLP-1 receptor and the glucagon receptor in vitro, compared to native oxyntomodulin, suggesting that these oxyntomodulin analogs are highly effective in treating diabetes, diabesity or diabetic complications, compared to native oxyntomodulin.

Example 3: Preparation of a Conjugate Comprising Oxyntomodulin Analog (SEQ ID NO: 23) and Immunoglobulin Fc (Immunoglobulin Fc-Conjugated Oxyntomodulin Analog 23)

In order to PEGylate MAL-10K-ALD PEG (NOF., Japan) at a cysteine residue at position 24 of the amino acid sequence of the oxyntomodulin analog (SEQ ID NO: 23), the oxyntomodulin analog (SEQ ID NO: 23) and MAL-10K-ALD PEG were allowed to react with each other at a molar ratio of 1:3 at a protein concentration of 3 mg/Mg at room temperature for 3 hours. The reaction was performed in 50 mM Tris buffer (pH 8.0) containing 1M guanidine. After completion of the reaction, the reaction solution was applied to SOURCE S under the following conditions, thereby purifying an oxyntomodulin analog mono-PEGylated at the cysteine: column: SOURCE S, flow rate: 2.0 Ml/min, gradient: A 0→100% 50 min B (A: 20 mM Na-citrate (pH 3.0)+45% ethanol, B: A+1M KCl).

Then, the purified mono-pegylated oxyntomodulin analog (SEQ ID NO: 23) and an immunoglobulin Fc were allowed to react with each other at a molar ratio of 1:5 at a protein concentration of 20 mg/Ml at 4° C. for 16 hours. The reaction was performed in 100 mM potassium phosphate buffer (pH 6.0) containing 20 mM SCB as a reducing agent. After completion of the reaction, the reaction solution was applied to a SOURCE purification column (column: SOURCE 15Q, flow rate: 2.0 Ml/min, gradient: A 0→4% 1 min, B→20% 80 min B (A: 20 mM Tris-HCl, pH 7.5, B: A+1M NaCl)) and a Source ISO column (column: SOURCE ISO, flow rate: 2.0 Ml/min, gradient: B 0→100% 100 min A, (A: 20 mM Tris-HCl, pH 7.5, B: A+1.1M AS)), thereby purifying a conjugate comprising the oxyntomodulin analog (SEQ ID NO: 23) and the immunoglobulin Fc.

Example 4: Preparation of a Conjugate Comprising Oxyntomodulin Analog (SEQ ID NO: 25) and Immunoglobulin Fc (Immunoglobulin Fc-Conjugated Oxyntomodulin Analog 25)

In order to PEGylate MAL-10K-ALD PEG at a cysteine residue at position 30 of the amino acid sequence of an oxyntomodulin analog (SEQ ID NO: 25), the oxyntomodulin analog (SEQ ID NO: 25) and MAL-10K-ALD PEG were allowed to react with each other at a molar ratio of 1:3 at a protein concentration of 3 mg/Ml at room temperature for 3 hours. The reaction was performed in 50 mM Tris buffer (pH 8.0) containing 1M guanidine. After completion of the reaction, the reaction solution was applied to SOURCE S under the following conditions, thereby purifying an oxyntomodulin analog mono-PEGylated at the cysteine: column: SOURCE S, flow rate: 2.0 Ml/min, gradient: A 0→100% 50 min B (A: 20 mM Na-citrate (pH 3.0)+45% ethanol, B: A+1M KCl).

Then, the purified mono-PEGylated oxyntomodulin analog (SEQ ID NO: 25) and an immunoglobulin Fc were allowed to react with each other at a molar ratio of 1:5 at a protein concentration of 20 mg/Ml at 4° C. for 16 hours. The reaction was performed in 100 mM potassium phosphate buffer (pH 6.0) containing 20 mM SCB as a reducing agent. After completion of the reaction, the reaction solution was applied to a SOURCE 15Q column (column: SOURCE 15Q, flow rate: 2.0 Ml/min, gradient: A 0→4% 1 min B→20% 80 min B (A: 20 mM Tris-HCl (pH 7.5), B: A+1M NaCl)) and a Source ISO column (column: SOURCE ISO, flow rate: 2.0 Ml/min, flow rate: B 0→100% 100 min A (A: 20 mM Tris-HCl (pH 7.5), B: A+1.1M AS)), thereby purifying a conjugate comprising the oxyntomodulin analog (SEQ ID NO: 25) and the immunoglobulin Fc.

Example 5: Preparation of a Conjugate Comprising Oxyntomodulin Analog (SEQ ID NO: 27) and Immunoglobulin Fc (Immunoglobulin Fc-Conjugated Oxyntomodulin Analog 27)

In order to PEGylate MAL-10K-ALD PEG at a cysteine residue at position 30 of the amino acid sequence of an oxyntomodulin analog (SEQ ID NO: 27), the oxyntomodulin analog (SEQ ID NO: 27) and MAL-10K-ALD PEG were allowed to react with each other at a molar ratio of 1:3 at a protein concentration of 3 mg/Ml at room temperature for 3 hours. The reaction was performed in 50 mM Tris buffer (pH 8.0) containing 1M guanidine. After completion of the reaction, the reaction solution was applied to SOURCE S under the following conditions, thereby obtaining an oxyntomodulin analog mono-PEGylated at the cysteine: column: SOURCE S, flow rate: 2.0 Ml/min, gradient: A 0→100% 50 min B (A: 20 mM Na-citrate (pH 3.0)+45% ethanol, B: A+1M KCl).

Then, the purified mono-PEGylated oxyntomodulin analog (SEQ ID NO: 27) and an immunoglobulin Fc were allowed to react with each other at a molar ratio of 1:5 at a protein concentration of 20 mg/Ml at 4° C. for 16 hours. The reaction was performed in 100 mM potassium phosphate buffer (pH 6.0) containing 20 mM SCB as a reducing agent. After completion of the reaction, the reaction solution was applied to a SOURCE 15Q column (column: SOURCE 15Q, flow rate: 2.0 Ml/min, gradient: A 0→4% 1 min B→20% 80 min B (A: 20 mM Tris-HCl (pH 7.5), B: A+1M NaCl)) and a Source ISO column (column: SOURCE ISO, flow rate: 2.0 Ml/min, gradient: B 0→100% 100 min A (A: 20 mM Tris-HCl (pH 7.5), B: A+1.1M AS)), thereby purifying a conjugate comprising the oxyntomodulin analog (SEQ ID NO: 27) and the immunoglobulin Fc.

Example 6: Effects of Long-Acting Oxyntomodulin Analog on Reduction in the Body Weight and Blood Glucose Level of High-Fat Diet-Induced Obesity (HF DIO) Mice

Example 6-1: Experimental Method

6-Week-old mice (C57BL/6, 120-130 g) were purchased from OrientBIO (Korea). The purchased C57BL/6 mice are animals that are widely used in studies on obesity and diabetes, because obesity therein can be relatively easily induced by high-fat diet. HF DIO mice are rodents that are frequently used in diabetes studies, and naturally show obesity and diabetic conditions similar to those of humans as a result of transplanting a high-fat diet into the organ without genetic manipulation, unlike db/db mice with diabetes induced by a mutation in the leptin receptor. For this reason, in the present invention, these animals were used to examine the effects of the composition of the present invention on reductions in body weight and blood glucose levels in diabesity.

The animals were allowed access to a high-fat diet (60% Kcal from fat diet, D12492; Research Diets Inc.) sterilized by UV irradiation. Also, the animals were allowed access to filtered and UV-sterilized tap water using water bottles. The animals were kept in a breeding chamber satisfying GLP standards under a 12-hr light/12-hr dark cycle (lighting: am 6 to pm 6), and all the experimental procedures were performed according to the standard guideline for animal experiments. Drug administration was started after 26 weeks of obesity induction, and the animals were divided into five groups (n=6) as shown in Table 3 below.

TABLE 3

| Groups | Drugs administered | | Methods of administration |
|---|---|---|---|
| HF D10-induced group | Vehicle (PBS) | | S.C. Once a week |
| HF D10-induced plus drug-administered groups | VICTOZA ® 100 nmol/kg | | S.C. Once a day |
| | SEQ ID NO: 25-Fc conjugate 1 nmol/kg | S.C. | Once a week |
| | SEQ ID NO: 25-Fc conjugate 3 nmol/kg | | |
| | SEQ ID NO: 25-Fc conjugate 5 nmol/kg | | |

Specifically, group 1 (HF DIO-induced group, control group) was fed with high-fat feed and administered subcutaneously with 5 ml/kg (injection volume) of Dulbecco's phosphate buffered saline (DPBS, Sigma) once or more a week. For a blood glucose tolerance test, group 1 was administered subcutaneously with Dulbecco's phosphate buffered saline (DPBS, Sigma) at 24 hours before the test and fasted for 16 hours. The blood was collected from the tail portion to measure the fasting glucose level, and the blood glucose levels at 15 min, 30 min, 60 min, 90 min and 120 min after intra-abdominal administration of 1 g/kg of glucose were measured.

Group 2 (HF DIO-induced and 100 nmol/kg VICTOZA® administered group) was fed with high-fat diet to induce obesity andhyperglycemia, and then administered once a day subcutaneously with 5 ml/kg (injection volume) of commercially available VICTOZA® GSK). For a blood glucose tolerance test, group 2 was fasted for 16 hours before the test and administered subcutaneously with 100 nmol/kg of VICTOZA® at 4 hours before the test. The blood was collected from the tail portion to measure the fasting glucose level, and the blood glucose levels at 15 min, 30 min, 60 min, 90 min and 120 min after intra-abdominal administration of 1 g/kg of glucose were measured.

Group 3 (HF DIO-induced and 1 nmol/kg SEQ ID NO: 25-Fc conjugate-administered group) was fed with high-fat feed to induce obesity andhyperglycemia, and then administered subcutaneously once a week with 1 nmol/kg (injection volume of 5 ml/kg) of the SEQ ID NO: 25-Fc conjugate prepared in Example 4. For a blood glucose tolerance test, group 3 was fasted for 24 hours before the test and administered subcutaneously with 1 nmol/kg of the SEQ ID NO: 25-Fc conjugate at 24 hours before the test and fasted for 16 hours. The blood was collected from the tail portion to measure the fasting glucose level, and the blood glucose levels at 15 min, 30 min, 60 min, 90 min and 120 min after intra-abdominal administration of 1 g/kg of glucose were measured.

Group 4 (HF DIO-induced and 3 nmol/kg SEQ ID NO: 25-Fc conjugate-administered group) was fed with high-fat feed to induce obesity andhyperglycemia, and then administered subcutaneously once a week with 3 nmol/kg (injection volume of 5 ml/kg) of the SEQ ID NO: 25-Fc conjugate prepared in Example 4. For a blood glucose tolerance test, group 3 was fasted for 24 hours before the test and administered subcutaneously with 3 nmol/kg of the SEQ ID NO: 25-Fc conjugate at 24 hours before the test and fasted for 16 hours. The blood was collected from the tail portion to measure the fasting glucose level, and the blood glucose levels at 15 min, 30 min, 60 min, 90 min and 120 min after intra-abdominal administration of 1 g/kg of glucose were measured.

Group 5 (HF DIO-induced and 5 nmol/kg SEQ ID NO: 25-Fc conjugate-administered group) was fed with high-fat feed to induce obesity andhyperglycemia, and then administered subcutaneously once a week with 5 nmol/kg (injection volume of 5 ml/kg) of the SEQ ID NO: 25-Fc conjugate prepared in Example 4. For a blood glucose tolerance test, group 3 was fasted for 24 hours before the test and administered subcutaneously with 5 nmol/kg of the SEQ ID NO: 25-Fc conjugate at 24 hours before the test and fasted for 16 hours. The blood was collected from the tail portion to measure the fasting glucose level, and the blood glucose levels at 15 min, 30 min, 60 min, 90 min and 120 min after intra-abdominal administration of 1 g/kg of glucose were measured.

For all the groups (n=6), saline or each drug was administered for 2 weeks, and then the effects thereof on reductions in the body weight and the blood glucose level were analyzed.

Example 6-2: Effects of Long-Acting Oxyntomodulin Analog on Reductions in Body Weight and Blood Glucose Level of High-Fat Diet-Induced Obesity (HF DIO) Mice which are Stable Obesity Models In order to examine the effect of the long-lasting oxyntomodulin analog of the present invention on a reduction in the blood glucose level of high-fat diet-induced (for 26 weeks) obesity (HF DIO) mice which are stable obesity models, the DIO mice classified in Example 6-1 were administered subcutaneously with the long-acting oxyntomodulin analog once a week for 2 weeks. The body weight and the feed intake were measured every day, and the blood was collected from the tail portion of the DIO mice at days 0, 3, 7, 10 and 14, and the change in the blood glucose levels was analyzed using HITACHI 7020. The changes in the body weight and the blood glucose level are shown in FIGS. 1 and 2.

Figure 2:
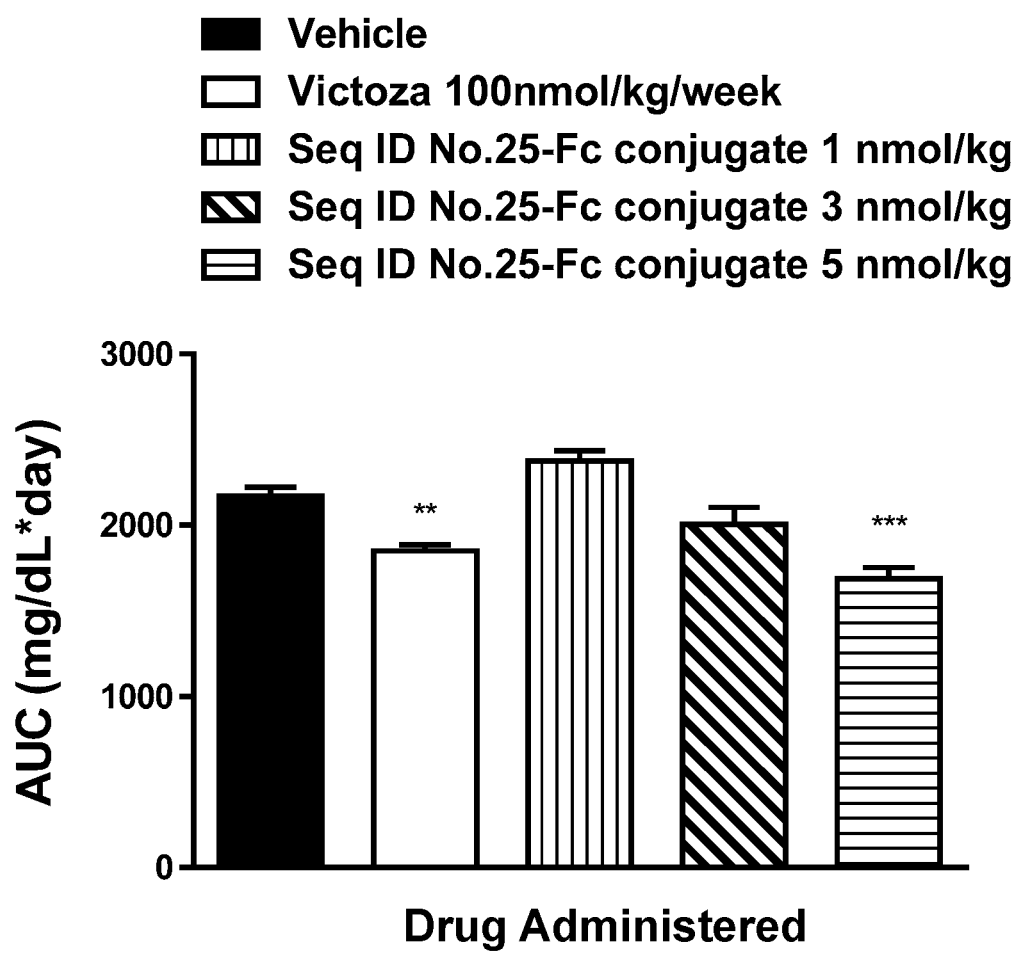
FIG. 2 is a graphic diagram showing an AUC (area under curve) for the change in blood glucose level caused by administration of a long-acting oxyntomodulin analog in mice with obesity induced by high-fat diet for a long period of time (26 weeks).

FIG. 1 shows the change in the body weight, and FIG. 2 shows the blood glucose AUC (area under curve). The obtained results were statistically processed, and the mean values and the standard deviations of the mean values were calculated.

In the verification of significance between the groups (n=6), data were statistically processed using Dunnett's test of one-way ANOVA, and a value of $p<0.05$ was considered statistically significant.

Specifically, the results of measurement of the change in the body weight indicated that the body weight of the mice with obesity induced by high-fat diet for 26 weeks did not decrease, whereas, when the mice with obesity were administered with the long-acting oxyntomodulin analog (SEQ ID NO: 25-Fc conjugate), the body weight thereof decreased in a dose-dependent manner (FIG. 1).

The results of measurement of the blood glucose level indicated that the blood glucose level of the mice with obesity decreased in a dose-dependent manner, when the mice were administered with the long-acting oxyntomodulin analog (SEQ ID NO: 25-Fc conjugate). Particularly, when the mice with obesity were administered with 5 nmol/kg of the long-acting oxyntomodulin analog (SEQ ID NO: 25-Fc conjugate), the blood glucose level thereof significantly decreased compared to that of the high-fat diet-induced DIO mice, and the blood glucose lowering effect of 5 nmol/kg of the long-acting oxyntomodulin analog (SEQ ID NO: 25-Fc conjugate) was equal to or better than that of VICTOZA® that is a commercially available drug for treating diabetes (FIG. 2).

From the results of Example 6-2, it was found that the long-acting oxyntomodulin analog conjugate of the present invention, which comprises the oxyntomodulin analog covalently linked to the immunoglobulin Fc region by PEG, reduced the body weight and blood glucose level of the high-fat diet-induced obesity (HF DIO) mice, suggesting that it can be effectively used for the treatment of diabetes, diabesity or related diseases.

Example 7: Effects of Long-Acting Oxyntomodulin Analog on Reductions in the Body Weight and Blood Glucose Level of db/db Mice with Diabetes Induced by Mutation in Leptin Receptor Example 7-1: Experimental Method 7-week old male BKS.Cg-+Lepr$^{db}$/+Lepr$^{db}$/OlaHsd mice (25±3 g, Harlan U.S.A) were purchased from Doo Yeol Biotech (Korea). BKS.Cg-+Lepr$^{db}$/+Lepr$^{db}$/OlaHsd mice (hereinafter referred to as db/db mice) are rodents that are most frequently used in diabetes studies together with ob/ob mice, and these mice naturally show diabetic conditions similar to those of humans through a mutation in the leptin receptor. For this reason, in the present invention, these animals were used to examine the blood glucose lowering effect of the agent of the present invention in the development of an agent for treating diabetes.

The purchased animals were acclimated and adapted to the experimental environment for 1 week, and then randomly grouped according to their glucose levels.

The animals were allowed access to solid feed (Picolab Rodent diet 5053) sterilized by UV irradiation. Also, the animals were allowed access to filtered and UV-sterilized tap water using water bottles. The animals were kept in a breeding chamber satisfying GLP standards under a 12-hr light/12-hr dark cycle (lighting: 6 a.m. to 6 p.m.), and all the experimental procedures were performed according to the standard guideline for animal experiments. The animals were divided into four groups (n=7) and administered with drugs as shown in Table 4 below.

TABLE 4

| Groups | Drugs administered | | Methods of administration |
|---|---|---|---|
| Control group | Vehicle (PBS) | S.C. | Once a week x 4 |
| Groups administered with drugs | VICTOZA ® 60 nmol/kg | S.C. | Once a day x 28 |
| Groups administered with drugs | VICTOZA ® 100 nmol/kg | | Once a day x 28 |
| Groups administered with drugs | SEQ ID NO: 23-Fc conjugate 15 nmol/kg | S.C. | Once a week x 4 |
| Groups administered with drugs | SEQ ID NO: 25-Fc conjugate 6 nmol/kg | | Once a week x 4 |

TABLE 4-continued

| Groups | Drugs administered | Methods of administration |
|---|---|---|
| Groups administered with drugs | | Once a week x 4 |

Specifically, group 1 (vehicle), a control group, was administered subcutaneously with 5 ml/kg of Dulbecco's phosphate buffered saline (DPBS, Sigma) once a week.

Group 2 (administered with 60 nmol/kg of VICTOZA®, a drug-administered group, was administered subcutaneously once a day with 60 nmol/kg (dose for diabetes; injection volume of 5 ml/kg) of commercially available Victoza® (GSK).

Group (administered with 100 nmol/kg of VICTOZA®, a drug-administered group, was administered subcutaneously once a day with 100 nmol/kg (dose for obesity; injection volume of 5 ml/kg) of commercially available Victoza® (GSK).

Group 4 (15 nmol/kg of SEQ ID NO: 23-Fc conjugate), a drug-administered group, was administered subcutaneously once a week with 15 nmol/kg (injection volume of 5 ml/kg) of the SEQ ID NO: 23-Fc conjugate prepared in Example 4.

Group 5 (6 nmol/kg of SEQ ID NO: 25-Fc conjugate), a drug-administered group, was administered subcutaneously once a week with 6 nmol/kg (injection volume of 5 ml/kg) of the SEQ ID NO: 25-Fc conjugate prepared in Example 4.

For all the groups (n=7), saline or each drug was administered for 4 weeks, and then the effects thereof on reductions in the body weight and the blood glucose level were analyzed.

Example 7-2: Analysis of the Effects of Long-Acting Oxyntomodulin Analog on Reductions in the Body Weight and Blood Glucose Level of db/db Mice with Diabetes by Mutation in Leptin Receptor In order to examine the effect of the long-acting oxyntomodulin analog of the present invention on a reduction in the blood glucose level of db/db mice with diabetes induced by a mutation in the leptin receptor, the db/db mice classified in Example 7-1 were administered subcutaneously with the long-acting oxyntomodulin analog once a week for 4 weeks. The change in the body weight of the mice was measured twice a week, and the blood was collected from the tail portion of the db/db mice (every day at weeks 1 and 4, and twice a week at weeks 2 and 3), and the change in the blood glucose level was analyzed using HITACHI 7020.

Figure 3:
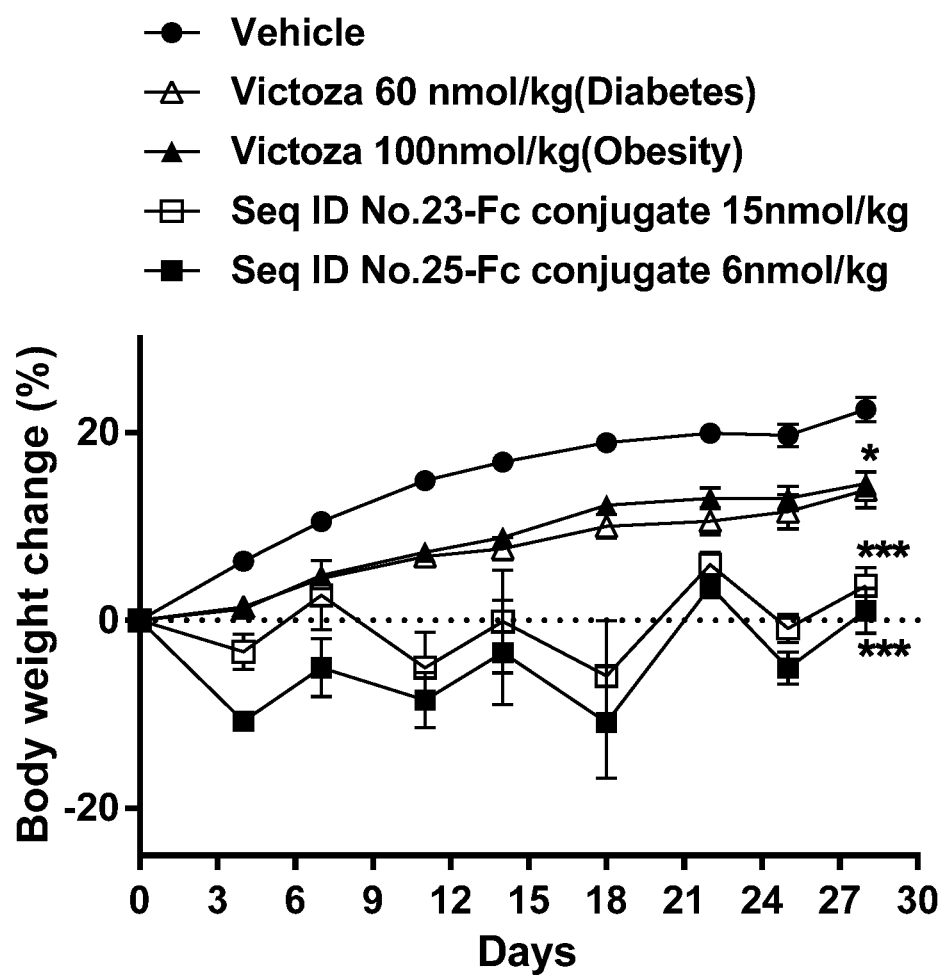
FIG. 3 is a graphic diagram showing the 4-week change in body weight caused by 4-week administration of a long-acting oxyntomodulin analog in a mouse model with diabetes induced by a mutation in the leptin receptor.
Figure 4:
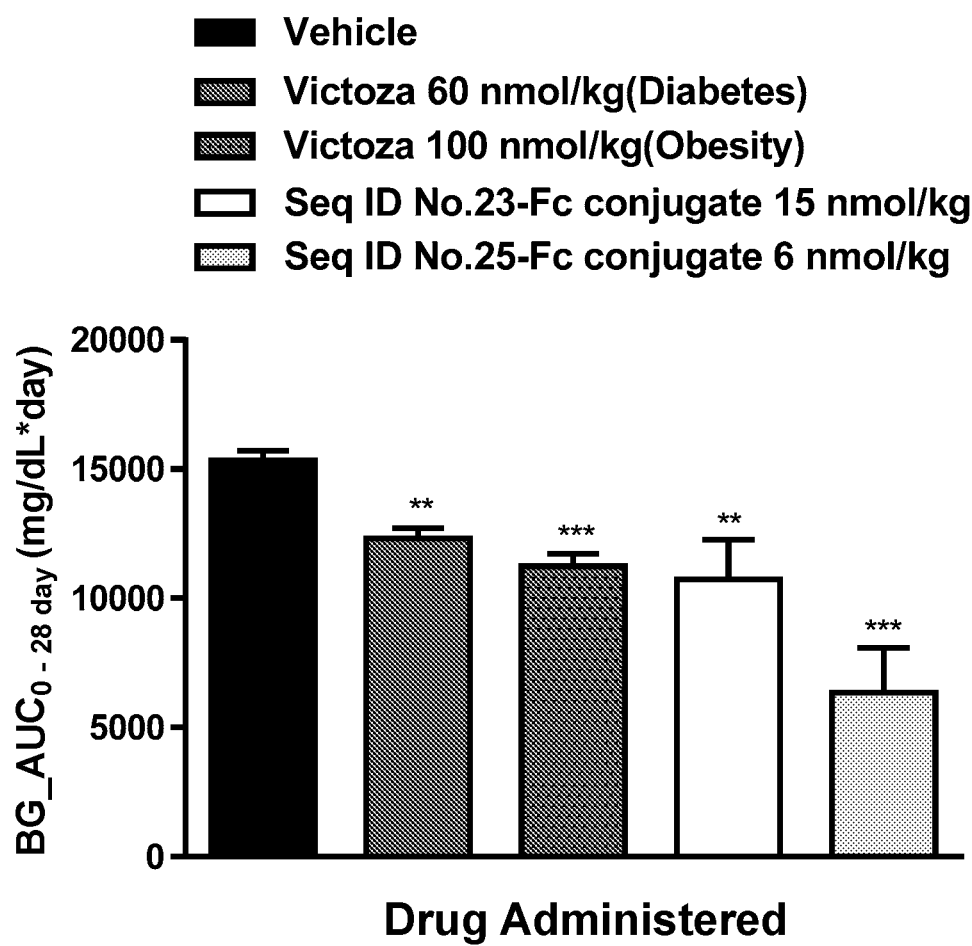
FIG. 4 is a graphic diagram showing an AUC (area under curve) for the change in blood glucose level caused by 4-week administration of a long-acting oxyntomodulin analog in a mouse model with diabetes induced by a mutation in the leptin receptor.

FIG. 3 shows the change in the body weight, and FIG. 4 shows the blood glucose AUC (area under curve). The obtained results were statistically processed, and the mean values and the standard deviations of the mean values were calculated. In the verification of significance between the groups (n=6), data were statistically processed using Dunnett's test of one-way ANOVA, and a value of $p<0.05$ was considered statistically significant.

Specifically, the results of measurement of the change in the body weight indicated that the body weight of the db/db mouse control group continuously increased from the day of start of administration, whereas, when the mice were administered with the long-acting oxyntomodulin analog (the SEQ ID NO: 23-Fc conjugate or the SEQ ID NO: 25-Fc conjugate), the body weight did not substantially change from the body weight measured at the day of state of administration, suggesting that the conjugate showed a significant effect of inhibiting the increase in the body weight (FIG. 3).

The results of measurement of the blood glucose level indicated that, when the mice were administered with the long-acting oxyntomodulin analog (the SEQ ID NO: 23-Fc conjugate or the SEQ ID NO: 25-Fc conjugate), the blood glucose level significantly decreased compared to that of the control group. Particularly, administration of 6 nmol/kg of the long-acting oxyntomodulin analog (SEQ ID NO: 25-Fc conjugate) showed a blood glucose lowering effect compared to that of VICTOZA® that is a commercially available drug for treating diabetes (FIG. 4).

From the results of Example 7, it was found that the long-acting oxyntomodulin analog of the present invention, which comprises the oxyntomodulin analog covalently linked to the immunoglobulin Fc region by PEG, significantly reduced the blood glucose level (index of diabetes) in the db/db mice with diabetes induced by the mutation in the leptin receptor, compared to the vehicle and VICTOZA® that is being used as a drug for treating diabetes, suggesting that the long-acting oxyntomodulin analog of the present invention can be very effectively used for the treatment of diabetes. In addition, the long-acting oxyntomodulin analog of the present invention showed a significant effect of inhibiting the increase in the body weight, suggesting that it can reduce diabetic cardiovascular complications.

From the results of Examples 6 and 7, it was seen that the long-lasting oxyntomodulin analog conjugate of the present invention showed an excellent blood glucose-lowering effect equal to or better than VICTOZA® known to have a blood glucose lowering effect, as well as an excellent body weight-reducing effect, suggesting that the long-lasting oxyntomodulin analog conjugate of the present invention can be effectively used as an agent for treating diabetes, diabesity and diabetic complications, by virtue of its blood level-lowering effect.

Those of ordinary skill in the art will recognize that the present invention may be embodied in other specific formed without departing from its spirit or essential characteristics. The described embodiments are to be considered in all respects only as illustrative and not restrictive. The scope of the present invention is, therefore, indicated by the appended claims rather than by the foregoing description. All changes which come within the meaning and range of equivalency of the claims are to be embraced within the scope of the present invention.

The invention claimed is:

1. A method for treating type II diabetes or diabesity, the method comprising administering a pharmaceutically effective amount of an oxyntomodulin analog conjugate to a subject in need thereof, wherein the oxyntomodulin analog conjugate comprises:
   an oxyntomodulin analog comprising the amino acid sequence of SEQ ID NO: 24, 25, or 26;
   an immunoglobulin Fc region; and
   a non-peptidyl polymer, wherein the non-peptidyl polymer covalently links the oxyntomodulin analog and the immunoglobulin Fc region.

2. The method of claim 1, wherein the oxyntomodulin analog comprises the amino acid sequence of SEQ ID NO: 24.

3. The method of claim 1, wherein the amino acids at positions 12 and 16 or 16 and 20 of the oxyntomodulin analog form a ring.

4. The method of claim 3, wherein the oxyntomodulin analog comprises the amino acid sequence of SEQ ID NO: 25.

5. The method of claim 3, wherein the oxyntomodulin analog comprises the amino acid sequence of SEQ ID NO: 26.

6. The method of claim 1, wherein the non-peptidyl polymer comprises polyethylene glycol, polypropylene glycol, an ethylene glycol/propylene glycol copolymer, a polyoxyethylated polyol, polyvinyl alcohol, a polysaccharide, polyvinyl ethyl ether, polylactic acid, polylactic-glycolic acid, a lipid polymer, hyaluronic acid, or a combination thereof.

7. The method of claim 6, wherein the non-peptidyl polymer is polyethylene glycol.

8. The method of claim 6, wherein the polysaccharide is dextran, a chitin, or a combination thereof.

9. The method of claim 1, wherein one end of the non-peptidyl polymer is linked to an amine group or a thiol group of the immunoglobulin Fc region and the other end of the non-peptidyl polymer is linked to an amine group or a thiol group of the oxyntomodulin analog.

10. The method of claim 1, wherein the method is for treating type II diabetes.

* * * * *

SEQUENCE LISTING

```
<160> NUMBER OF SEQ ID NOS: 59

<210> SEQ ID NO 1
<211> LENGTH: 37
<212> TYPE: PRT
<213> ORGANISM: Homo sapiens
<220> FEATURE:
<221> NAME/KEY: MISC_FEATURE
<222> LOCATION: (1)..(37)
<223> OTHER INFORMATION: Oxyntomodulin

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 2

His Ser Gln Gly Thr Phe Thr Ser Asp Tyr Ser Lys Tyr Leu Asp Glu
1               5                   10                  15

Glu Ala Val Arg Leu Phe Ile Glu Trp Leu Met Asn Thr Lys Arg Asn
            20                  25                  30

Arg Asn Asn Ile Ala
        35
```

```
<210> SEQ ID NO 3
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 3

His Ser Gln Gly Thr Phe Thr Ser Asp Tyr Ser Lys Tyr Leu Asp Glu
1               5                   10                  15

Arg Arg Ala Gln Asp Phe Val Ala Trp Leu Lys Asn Thr Gly Pro Ser
            20                  25                  30

Ser Gly Ala Pro Pro Pro Ser
        35

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 4

His Gly Gln Gly Thr Phe Thr Ser Asp Tyr Ser Arg Tyr Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 5
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 5

His Gly Gln Gly Thr Phe Thr Ser Asp Tyr Ser Arg Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 6
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
```

```
<220> FEATURE:
<221> NAME/KEY: MOD_RES
<222> LOCATION: (1)..(1)
<223> OTHER INFORMATION: 4-imidazoacetyl

<400> SEQUENCE: 6

His Gly Glu Gly Thr Phe Thr Ser Asp Leu Ser Arg Gln Met Glu Glu
1               5                   10                  15

Glu Ala Val Arg Leu Phe Ile Glu Trp Ala Ala His Ser Gln Gly Thr
            20                  25                  30

Phe Thr Ser Asp Tyr Ser Lys Tyr Leu Asp
        35                  40

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 7

His Ser Gln Gly Thr Phe Thr Ser Asp Tyr Ser Arg Tyr Leu Asp Glu
1               5                   10                  15

Glu Ala Val Arg Leu Phe Ile Glu Trp Leu Met Asn Thr Lys
            20                  25                  30

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 8

His Ser Gln Gly Thr Phe Thr Ser Asp Leu Ser Arg Gln Leu Glu Glu
1               5                   10                  15

Glu Ala Val Arg Leu Phe Ile Glu Trp Leu Met Asn Lys
            20                  25

<210> SEQ ID NO 9
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (20)..(20)
<223> OTHER INFORMATION: Alpha-methyl-glutamic acid
```

```
<400> SEQUENCE: 9

His Gly Gln Gly Thr Phe Thr Ser Asp Tyr Ser Arg Tyr Leu Asp Glu
1               5                   10                  15

Glu Ala Val Glu Leu Phe Ile Glu Trp Leu Met Asn Thr Lys Arg Asn
            20                  25                  30

Arg Asn Asn Ile Ala
        35

<210> SEQ ID NO 10
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 10

His Ser Gln Gly Thr Phe Thr Ser Asp Tyr Ser Arg Gln Met Glu Glu
1               5                   10                  15

Glu Ala Val Arg Leu Phe Ile Glu Trp Leu Met Asn Gly Gly Pro Ser
            20                  25                  30

Ser Gly Ala Pro Pro Pro Ser Lys
        35                  40

<210> SEQ ID NO 11
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 11

His Gly Glu Gly Thr Phe Thr Ser Asp Leu Ser Arg Gln Met Glu Glu
1               5                   10                  15

Glu Ala Val Arg Leu Phe Ile Glu Trp Ala Ala His Ser Gln Gly Thr
            20                  25                  30

Phe Thr Ser Asp Tyr Ser Arg Tyr Leu Asp Lys
        35                  40

<210> SEQ ID NO 12
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
```

```
<400> SEQUENCE: 12

His Ser Gln Gly Thr Phe Thr Ser Asp Tyr Ser Arg Tyr Leu Asp Gly
1               5                   10                  15
Gly Gly His Gly Glu Gly Thr Phe Thr Ser Asp Leu Ser Lys Gln Met
            20                  25                  30
Glu Glu Glu Ala Val Lys
        35

<210> SEQ ID NO 13
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (16)..(16)
<223> OTHER INFORMATION: Alpha-methyl-glutamic acid
<220> FEATURE:
<221> NAME/KEY: MOD_RES
<222> LOCATION: (20)..(20)
<223> OTHER INFORMATION: Alpha-methyl-glutamic acid

<400> SEQUENCE: 13

His Ser Gln Gly Thr Phe Thr Ser Asp Tyr Ser Arg Tyr Leu Asp Glu
1               5                   10                  15
Glu Ala Val Glu Leu Phe Ile Glu Trp Leu Met Asn Thr Lys
            20                  25                  30

<210> SEQ ID NO 14
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (20)..(20)
<223> OTHER INFORMATION: Alpha-methyl-glutamic acid
<220> FEATURE:
<221> NAME/KEY: MOD_RES
<222> LOCATION: (24)..(24)
<223> OTHER INFORMATION: Alpha-methyl-glutamic acid

<400> SEQUENCE: 14

His Gly Gln Gly Thr Phe Thr Ser Asp Tyr Ser Arg Tyr Leu Asp Glu
1               5                   10                  15
Glu Ala Val Glu Leu Phe Ile Glu Trp Leu Met Asn Thr Lys Arg Asn
            20                  25                  30
Arg Asn Asn Ile Ala
        35

<210> SEQ ID NO 15
<211> LENGTH: 37
<212> TYPE: PRT
<213> ORGANISM: Artificial Sequence
```

```
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (24)..(24)
<223> OTHER INFORMATION: Alpha-methyl-glutamic acid

<400> SEQUENCE: 15

His Gly Gln Gly Thr Phe Thr Ser Asp Tyr Ser Arg Tyr Leu Asp Glu
1               5                   10                  15

Glu Ala Val Arg Leu Phe Ile Glu Trp Leu Met Asn Thr Lys Arg Asn
            20                  25                  30

Arg Asn Asn Ile Ala
            35

<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 16

His Ser Gln Gly Thr Phe Thr Ser Asp Leu Ser Arg Gln Leu Glu Gly
1               5                   10                  15

Gly Gly His Ser Gln Gly Thr Phe Thr Ser Asp Leu Ser Arg Gln Leu
            20                  25                  30

Glu Lys

<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 17

His Ser Gln Gly Thr Phe Thr Ser Asp Tyr Ser Arg Tyr Leu Asp Glu
1               5                   10                  15

Glu Ala Val Arg Leu Phe Ile Glu Trp Ile Arg Asn Thr Lys Arg Asn
            20                  25                  30

Arg Asn Asn Ile Ala
            35

<210> SEQ ID NO 18
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
```

```
<220> FEATURE:
<221> NAME/KEY: MOD_RES
<222> LOCATION: (1)..(1)
<223> OTHER INFORMATION: 4-imidazoacetyl

<400> SEQUENCE: 18

His Ser Gln Gly Thr Phe Thr Ser Asp Tyr Ser Arg Tyr Leu Asp Glu
1               5                   10                  15

Glu Ala Val Arg Leu Phe Ile Glu Trp Ile Arg Asn Gly Gly Pro Ser
            20                  25                  30

Ser Gly Ala Pro Pro Pro Ser Lys
        35                  40

<210> SEQ ID NO 19
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MISC_FEATURE
<222> LOCATION: (16)..(20)
<223> OTHER INFORMATION: Ring formation between residues

<400> SEQUENCE: 19

His Ser Gln Gly Thr Phe Thr Ser Asp Tyr Ser Arg Tyr Leu Asp Glu
1               5                   10                  15

Glu Ala Val Lys Leu Phe Ile Glu Trp Ile Arg Asn Thr Lys Arg Asn
            20                  25                  30

Arg Asn Asn Ile Ala
        35

<210> SEQ ID NO 20
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MISC_FEATURE
<222> LOCATION: (16)..(20)
<223> OTHER INFORMATION: Ring formation between residues

<400> SEQUENCE: 20

His Ser Gln Gly Thr Phe Thr Ser Asp Tyr Ser Arg Tyr Leu Asp Glu
1               5                   10                  15

Glu Ala Val Lys Leu Phe Ile Glu Trp Ile Arg Asn Gly Gly Pro Ser
            20                  25                  30

Ser Gly Ala Pro Pro Pro Ser Lys
        35                  40

<210> SEQ ID NO 21
<211> LENGTH: 37
<212> TYPE: PRT
<213> ORGANISM: Artificial Sequence
```

```
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 21

His Ser Gln Gly Thr Phe Thr Ser Asp Tyr Ser Arg Gln Leu Glu Glu
1               5                   10                  15

Glu Ala Val Arg Leu Phe Ile Glu Trp Val Arg Asn Thr Lys Arg Asn
                20                  25                  30

Arg Asn Asn Ile Ala
                35

<210> SEQ ID NO 22
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: Desamino-histidyl
<220> FEATURE:
<221> NAME/KEY: MISC_FEATURE
<222> LOCATION: (16)..(20)
<223> OTHER INFORMATION: Ring formation between residues

<400> SEQUENCE: 22

His Ser Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Lys
                20                  25                  30

<210> SEQ ID NO 23
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide construct of Oxyntomodulin derivative
<220> FEATURE:
<221> NAME/KEY: MOD_RES
<222> LOCATION: (2)..(2)
<223> OTHER INFORMATION: Aib

<400> SEQUENCE: 23

His Xaa Gln Gly Thr Phe Thr Ser Asp Tyr Ser Lys Tyr Leu Asp Glu
1               5                   10                  15

Lys Arg Ala Lys Glu Phe Val Cys Trp Leu Met Asn Thr
                20                  25

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (2)..(2)
<223> OTHER INFORMATION: Aib
```

```
<400> SEQUENCE: 24

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 25

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (12)..(16)
<223> OTHER INFORMATION: Ring formation between residues

<400> SEQUENCE: 26

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 27
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide construct of Oxyntomodulin derivative
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues
```

```
<400> SEQUENCE: 27

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 28
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide construct of Oxyntomodulin derivative
<220> FEATURE:
<221> NAME/KEY: MOD_RES
<222> LOCATION: (2)..(2)
<223> OTHER INFORMATION: Aib

<400> SEQUENCE: 28

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr
            20                  25

<210> SEQ ID NO 29
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (2)..(2)
<223> OTHER INFORMATION: D-Ser

<400> SEQUENCE: 29

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 30
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 30

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35
```

```
<210> SEQ ID NO 31
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (2)..(2)
<223> OTHER INFORMATION: D-Ser

<400> SEQUENCE: 31

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 32
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 32

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 33
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide oxyntomodulin derivative
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues
```

```
<400> SEQUENCE: 33

His Xaa Gln Gly Thr Phe Thr Ser Asp Tyr Ala Lys Tyr Leu Asp Glu
1               5                   10                  15

Lys Arg Ala Lys Glu Phe Val Gln Trp Leu Met Asn Thr Cys
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide oxyntomodulin derivative
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 34

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide construct of group R2

<400> SEQUENCE: 35

Lys Arg Asn Arg Asn Asn Ile Ala
1               5

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide construct of group R2

<400> SEQUENCE: 36

Gly Pro Ser Ser Gly Ala Pro Pro Pro Ser
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide construct of group R2

<400> SEQUENCE: 37

Gly Pro Ser Ser Gly Ala Pro Pro Pro Ser Lys
1               5                   10
```

```
<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide construct of group R2

<400> SEQUENCE: 38

His Ser Gln Gly Thr Phe Thr Ser Asp Tyr Ser Lys Tyr Leu Asp
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct of group R2

<400> SEQUENCE: 39

His Ser Gln Gly Thr Phe Thr Ser Asp Tyr Ser Arg Tyr Leu Asp Lys
1               5                   10                  15

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide construct of group R2

<400> SEQUENCE: 40

His Gly Glu Gly Thr Phe Thr Ser Asp Leu Ser Lys Gln Met Glu Glu
1               5                   10                  15

Glu Ala Val Lys
            20

<210> SEQ ID NO 41
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct of group A or B

<400> SEQUENCE: 41

Ser Gln Gly Thr Phe Thr Ser Asp Tyr Ser Lys Tyr Leu Asp Ser Arg
1               5                   10                  15

Arg Ala Gln Asp Phe Val Gln Trp Leu Met Asn Thr
            20                  25

<210> SEQ ID NO 42
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct of group A or B

<400> SEQUENCE: 42

Ser Gln Gly Thr Phe Thr Ser Asp Tyr Ser Lys Tyr Leu Asp Glu Glu
1               5                   10                  15

Ala Val Arg Leu Phe Ile Glu Trp Leu Met Asn Thr
            20                  25
```

```
<210> SEQ ID NO 43
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct of group A or B

<400> SEQUENCE: 43

Ser Gln Gly Thr Phe Thr Ser Asp Tyr Ser Lys Tyr Leu Asp Glu Arg
1               5                   10                  15

Arg Ala Gln Asp Phe Val Ala Trp Leu Lys Asn Thr
            20                  25

<210> SEQ ID NO 44
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct of group A or B

<400> SEQUENCE: 44

Gly Gln Gly Thr Phe Thr Ser Asp Tyr Ser Arg Tyr Leu Glu Glu Glu
1               5                   10                  15

Ala Val Arg Leu Phe Ile Glu Trp Leu Lys Asn Gly
            20                  25

<210> SEQ ID NO 45
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct of group A or B

<400> SEQUENCE: 45

Gly Gln Gly Thr Phe Thr Ser Asp Tyr Ser Arg Gln Met Glu Glu Glu
1               5                   10                  15

Ala Val Arg Leu Phe Ile Glu Trp Leu Lys Asn Gly
            20                  25

<210> SEQ ID NO 46
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide construct of group A or B

<400> SEQUENCE: 46

Gly Glu Gly Thr Phe Thr Ser Asp Leu Ser Arg Gln Met Glu Glu Glu
1               5                   10                  15

Ala Val Arg Leu Phe Ile Glu Trp Ala Ala
            20                  25

<210> SEQ ID NO 47
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct of group A or B
```

```
<400> SEQUENCE: 47

Ser Gln Gly Thr Phe Thr Ser Asp Tyr Ser Arg Gln Met Glu Glu
1               5                   10                  15

Ala Val Arg Leu Phe Ile Glu Trp Leu Met Asn Gly
            20                  25

<210> SEQ ID NO 48
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide construct of group B

<400> SEQUENCE: 48

Gly Glu Gly Thr Phe Thr Ser Asp Leu Ser Arg Gln Met Glu Glu
1               5                   10                  15

Ala Val Arg Leu Phe Ile Glu Trp
            20

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide construct of group B

<400> SEQUENCE: 49

Ser Gln Gly Thr Phe Thr Ser Asp Tyr Ser Arg Tyr Leu Asp
1               5                   10

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cccggccccc gcggccgcta ttcgaaatac                                      30

<210> SEQ ID NO 51
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gaacggtccg gaggacgtcg actcttaaga tag                                  33

<210> SEQ ID NO 52
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cagcgacacc gaccgtcccc ccgtacttaa ggcc                                 34
```

-continued

```
<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ctaaccgact ctcggggaag actgagctcg cc                                    32

<210> SEQ ID NO 54
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MOD_RES
<222> LOCATION: (2)..(2)
<223> OTHER INFORMATION: Aib (aminosiobutyric acid), d-alanine, glycine,
      Sar (N-methylglycine), serine or d-serine
<220> FEATURE:
<221> NAME/KEY: MOD_RES
<222> LOCATION: (3)..(3)
<223> OTHER INFORMATION: Glutamic acid or glutamine
<220> FEATURE:
<221> NAME/KEY: MOD_RES
<222> LOCATION: (10)..(10)
<223> OTHER INFORMATION: Leucine or tyrosine
<220> FEATURE:
<221> NAME/KEY: MOD_RES
<222> LOCATION: (11)..(11)
<223> OTHER INFORMATION: Serine or alanine
<220> FEATURE:
<221> NAME/KEY: MOD_RES
<222> LOCATION: (12)..(12)
<223> OTHER INFORMATION: Lysine or arginine
<220> FEATURE:
<221> NAME/KEY: MOD_RES
<222> LOCATION: (13)..(13)
<223> OTHER INFORMATION: Glutamine or tyrosine
<220> FEATURE:
<221> NAME/KEY: MOD_RES
<222> LOCATION: (14)..(14)
<223> OTHER INFORMATION: Leucine or methionine
<220> FEATURE:
<221> NAME/KEY: MOD_RES
<222> LOCATION: (15)..(15)
<223> OTHER INFORMATION: Aspartic acid or glutamic acid
<220> FEATURE:
<221> NAME/KEY: MOD_RES
<222> LOCATION: (16)..(16)
<223> OTHER INFORMATION: Glutamic acid, serine, alpha-methyl-glutamic
      acid or not present
<220> FEATURE:
<221> NAME/KEY: MOD_RES
<222> LOCATION: (17)..(17)
<223> OTHER INFORMATION: Glutamine, glutamic acid, lysine, arginine,
      serine or not present
<220> FEATURE:
<221> NAME/KEY: MOD_RES
<222> LOCATION: (18)..(18)
<223> OTHER INFORMATION: Alanine, arginine, valine or not present
<220> FEATURE:
<221> NAME/KEY: MOD_RES
<222> LOCATION: (19)..(19)
<223> OTHER INFORMATION: Alanine, arginine, serine, valine or not
      present
```

```
<220> FEATURE:
<221> NAME/KEY: MOD_RES
<222> LOCATION: (20)..(20)
<223> OTHER INFORMATION: Lysine, glutamine, arginine,
      alpha-methyl-glutamic acid or not present
<220> FEATURE:
<221> NAME/KEY: MOD_RES
<222> LOCATION: (21)..(21)
<223> OTHER INFORMATION: Aspartic acid, glutamic acid, leucine or not
      present
<220> FEATURE:
<221> NAME/KEY: MISC_FEATURE
<222> LOCATION: (22)..(22)
<223> OTHER INFORMATION: May or may not be present
<220> FEATURE:
<221> NAME/KEY: MOD_RES
<222> LOCATION: (23)..(23)
<223> OTHER INFORMATION: Isoleucine, valine or not present
<220> FEATURE:
<221> NAME/KEY: MOD_RES
<222> LOCATION: (24)..(24)
<223> OTHER INFORMATION: Alanine, cysteine, glutamic acid, lysine,
      glutamine, alpha-methyl-glutamic acid or not present
<220> FEATURE:
<221> NAME/KEY: MISC_FEATURE
<222> LOCATION: (25)..(25)
<223> OTHER INFORMATION: May or may not be present
<220> FEATURE:
<221> NAME/KEY: MOD_RES
<222> LOCATION: (26)..(26)
<223> OTHER INFORMATION: Alanine, isoleucine, leucine, serine, valine
      or not present
<220> FEATURE:
<221> NAME/KEY: MOD_RES
<222> LOCATION: (27)..(27)
<223> OTHER INFORMATION: Alanine, lysine, methionine, glutamine,
      arginine or not present
<220> FEATURE:
<221> NAME/KEY: MISC_FEATURE
<222> LOCATION: (28)..(28)
<223> OTHER INFORMATION: May or may not be present
<220> FEATURE:
<221> NAME/KEY: MOD_RES
<222> LOCATION: (29)..(29)
<223> OTHER INFORMATION: Alanine, glycine, threonine or not present
<220> FEATURE:
<221> NAME/KEY: MOD_RES
<222> LOCATION: (30)..(30)
<223> OTHER INFORMATION: Cysteine, lysine or not present
<220> FEATURE:
<221> NAME/KEY: MOD_RES
<222> LOCATION: (31)..(40)
<223> OTHER INFORMATION: Alanine, glycine, serine or not present
<220> FEATURE:
<221> NAME/KEY: MISC_FEATURE
<222> LOCATION: (31)..(40)
<223> OTHER INFORMATION: This region may encompass 2 to 10 amino acids,
      wherein some positions may be absent
<220> FEATURE:
<221> NAME/KEY: MISC_FEATURE
<222> LOCATION: (41)..(60)
<223> OTHER INFORMATION: This region may encompass 8 to 20 amino acids
      including "KRNRNNIA" or "GPSSGAPPPS" or "GPSSGAPPPSK" or
      "HSQGTFTSDYSKYLD" or "HSQGTFTSDYSRYLDK" or "HGEGTFTSDLSKQMEEEAVK,"
      wherein some or all positions may be absent
<220> FEATURE:
<223> OTHER INFORMATION: See specification as filed for detailed
      description of substitutions and preferred embodiments

<400> SEQUENCE: 54

Xaa Xaa Xaa Gly Thr Phe Thr Ser Asp Xaa Xaa Xaa Xaa Xaa Xaa
1               5                   10                  15

Xaa Xaa Xaa Xaa Xaa Phe Xaa Xaa Trp Xaa Xaa Asn Xaa Xaa Xaa Xaa
            20                  25                  30
```

```
Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa
        50                  55                  60

<210> SEQ ID NO 55
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl, 4-
      imidazoacetyl, beta-carboxy imidazopropionyl or tyrosine
<220> FEATURE:
<221> NAME/KEY: MISC_FEATURE
<222> LOCATION: (2)..(29)
<223> OTHER INFORMATION: This region may encompass 26 to 28 amino acids
      including "SQGTFTSDYSKYLDSRRAQDFVQWLMNT" or
      "SQGTFTSDYSKYLDEEAVRLFIEWLMNT" or "SQGTFTSDYSKYLDERRAQDFVAWLKNT"
      or "GQGTFTSDYSRYLEEEAVRLFIEWLKNG" or
      "GQGTFTSDYSRQMEEEAVRLFIEWLKNG"
<220> FEATURE:
<221> NAME/KEY: MISC_FEATURE
<222> LOCATION: (2)..(29)
<223> OTHER INFORMATION: Continued from above; or
      "GEGTFTSDLSRQMEEEAVRLFIEWAA" or "SQGTFTSDYSRQMEEEAVRLFIEWLMNG,"
      wherein some positions may be absent
<220> FEATURE:
<221> NAME/KEY: MISC_FEATURE
<222> LOCATION: (30)..(40)
<223> OTHER INFORMATION: This region may encompass 8 to 11 amino acids
      including "KRNRNNIA" or "GPSSGAPPPS" or "GPSSGAPPPSK," wherein
      some positions may be absent
<220> FEATURE:
<223> OTHER INFORMATION: See specification as filed for detailed
      description of substitutions and preferred embodiments

<400> SEQUENCE: 55

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
        20                  25                  30

Xaa Xaa Xaa Xaa Xaa Xaa Xaa Xaa
        35                  40

<210> SEQ ID NO 56
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl, 4-
      imidazoacetyl, beta-carboxy imidazopropionyl or tyrosine
<220> FEATURE:
<221> NAME/KEY: MISC_FEATURE
<222> LOCATION: (2)..(29)
<223> OTHER INFORMATION: This region may encompass 14 to 28 amino acids
      including "SQGTFTSDYSKYLDSRRAQDFVQWLMNT" or
      "SQGTFTSDYSKYLDEEAVRLFIEWLMNT" or "SQGTFTSDYSKYLDERRAQDFVAWLKNT"
      or "GQGTFTSDYSRYLEEEAVRLFIEWLKNG" or
      "GQGTFTSDYSRQMEEEAVRLFIEWLKNG"
```

```
<220> FEATURE:
<221> NAME/KEY: MISC_FEATURE
<222> LOCATION: (2)..(29)
<223> OTHER INFORMATION: Continued from above; or
      "GEGTFTSDLSRQMEEEAVRLFIEWAA" or "SQGTFTSDYSRQMEEEAVRLFIEWLMNG" or
      "GEGTFTSDLSRQMEEEAVRLFIEW" or "SQGTFTSDYSRYLD," wherein some
      positions may be absent
<220> FEATURE:
<221> NAME/KEY: MOD_RES
<222> LOCATION: (30)..(39)
<223> OTHER INFORMATION: Alanine, glycine, serine or not present
<220> FEATURE:
<221> NAME/KEY: MISC_FEATURE
<222> LOCATION: (30)..(39)
<223> OTHER INFORMATION: This region may encompass 2 to 10 amino acids,
      wherein some positions may be absent
<220> FEATURE:
<221> NAME/KEY: MISC_FEATURE
<222> LOCATION: (40)..(59)
<223> OTHER INFORMATION: This region may encompass 15 to 20 amino acids
      including "HSQGTFTSDYSKYLD" or "HSQGTFTSDYSRYLDK" or
      "HGEGTFTSDLSKQMEEEAVK," wherein some positions may be absent
<220> FEATURE:
<223> OTHER INFORMATION: See specification as filed for detailed
      description of substitutions and preferred embodiments

<400> SEQUENCE: 56

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa
    50                  55

<210> SEQ ID NO 57
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl, 4-
      imidazoacetyl, beta-carboxy imidazopropionyl or tyrosine
<220> FEATURE:
<221> NAME/KEY: MOD_RES
<222> LOCATION: (16)..(16)
<223> OTHER INFORMATION: Serine, glutamic acid or arginine
<220> FEATURE:
<221> NAME/KEY: MOD_RES
<222> LOCATION: (17)..(17)
<223> OTHER INFORMATION: Arginine, glutamic acid or serine
<220> FEATURE:
<221> NAME/KEY: MOD_RES
<222> LOCATION: (18)..(18)
<223> OTHER INFORMATION: Arginine, alanine or valine
<220> FEATURE:
<221> NAME/KEY: MOD_RES
<222> LOCATION: (19)..(19)
<223> OTHER INFORMATION: Arginine, valine or serine
<220> FEATURE:
<221> NAME/KEY: MOD_RES
<222> LOCATION: (20)..(20)
<223> OTHER INFORMATION: Glutamine, arginine or lysine
<220> FEATURE:
<221> NAME/KEY: MOD_RES
<222> LOCATION: (26)..(26)
<223> OTHER INFORMATION: Isoleucine, valine or serine
```

```
<220> FEATURE:
<221> NAME/KEY: MOD_RES
<222> LOCATION: (27)..(27)
<223> OTHER INFORMATION: Methionine, arginine or glutamine
<220> FEATURE:
<221> NAME/KEY: MOD_RES
<222> LOCATION: (29)..(29)
<223> OTHER INFORMATION: Threonine, glycine or alanine
<220> FEATURE:
<221> NAME/KEY: MISC_FEATURE
<222> LOCATION: (30)..(40)
<223> OTHER INFORMATION: This region may encompass 8 to 11 amino acids
      including "KRNRNNIA" or "GPSSGAPPPS" or "GPSSGAPPPSK," wherein
      some positions may be absent
<220> FEATURE:
<223> OTHER INFORMATION: See specification as filed for detailed
      description of substitutions and preferred embodiments

<400> SEQUENCE: 57

Xaa Ser Gln Gly Thr Phe Thr Ser Asp Tyr Ser Lys Tyr Leu Asp Xaa
1               5                   10                  15

Xaa Xaa Xaa Xaa Leu Phe Val Gln Trp Xaa Xaa Asn Xaa Xaa Xaa Xaa
            20                  25                  30

Xaa Xaa Xaa Xaa Xaa Xaa Xaa Xaa
        35                  40

<210> SEQ ID NO 58
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl, 4-
      imidazoacetyl, beta-carboxy imidazopropionyl or tyrosine
<220> FEATURE:
<221> NAME/KEY: MOD_RES
<222> LOCATION: (2)..(2)
<223> OTHER INFORMATION: Serine, Aib, Sarcosine, d-alanine or d-serine
<220> FEATURE:
<221> NAME/KEY: MOD_RES
<222> LOCATION: (16)..(16)
<223> OTHER INFORMATION: Serine or glutamic acid
<220> FEATURE:
<221> NAME/KEY: MOD_RES
<222> LOCATION: (17)..(17)
<223> OTHER INFORMATION: Arginine or lysine
<220> FEATURE:
<221> NAME/KEY: MOD_RES
<222> LOCATION: (20)..(20)
<223> OTHER INFORMATION: Glutamine or lysine
<220> FEATURE:
<221> NAME/KEY: MOD_RES
<222> LOCATION: (21)..(21)
<223> OTHER INFORMATION: Aspartic acid or glutamic acid
<220> FEATURE:
<221> NAME/KEY: MOD_RES
<222> LOCATION: (24)..(24)
<223> OTHER INFORMATION: Glutamine, cysteine or lysine
<220> FEATURE:
<221> NAME/KEY: MOD_RES
<222> LOCATION: (30)..(30)
<223> OTHER INFORMATION: Cysteine, lysine or not present
<220> FEATURE:
<221> NAME/KEY: MISC_FEATURE
<222> LOCATION: (31)..(41)
<223> OTHER INFORMATION: This region may encompass 8 to 11 amino acids
      including "KRNRNNIA" or "GPSSGAPPPS" or "GPSSGAPPPSK," wherein
      some or all positions may be absent
```

<220> FEATURE:
<223> OTHER INFORMATION: See specification as filed for detailed
      description of substitutions and preferred embodiments

<400> SEQUENCE: 58

Xaa Xaa Gln Gly Thr Phe Thr Ser Asp Tyr Ser Lys Tyr Leu Asp Xaa
1               5                   10                  15

Xaa Arg Ala Xaa Xaa Phe Val Xaa Trp Leu Met Asn Thr Xaa Xaa Xaa
            20                  25                  30

Xaa Xaa Xaa Xaa Xaa Xaa Xaa Xaa Xaa
        35                  40

<210> SEQ ID NO 59
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, 4-imidazoacetyl
      or tyrosine
<220> FEATURE:
<221> NAME/KEY: MOD_RES
<222> LOCATION: (2)..(2)
<223> OTHER INFORMATION: Aib (aminosiobutyric acid), glycine or serine
<220> FEATURE:
<221> NAME/KEY: MOD_RES
<222> LOCATION: (3)..(3)
<223> OTHER INFORMATION: Glutamic acid or glutamine
<220> FEATURE:
<221> NAME/KEY: MOD_RES
<222> LOCATION: (10)..(10)
<223> OTHER INFORMATION: Leucine or tyrosine
<220> FEATURE:
<221> NAME/KEY: MOD_RES
<222> LOCATION: (11)..(11)
<223> OTHER INFORMATION: Serine or alanine
<220> FEATURE:
<221> NAME/KEY: MOD_RES
<222> LOCATION: (12)..(12)
<223> OTHER INFORMATION: Lysine or arginine
<220> FEATURE:
<221> NAME/KEY: MOD_RES
<222> LOCATION: (13)..(13)
<223> OTHER INFORMATION: Glutamine or tyrosine
<220> FEATURE:
<221> NAME/KEY: MOD_RES
<222> LOCATION: (14)..(14)
<223> OTHER INFORMATION: Leucine or methionine
<220> FEATURE:
<221> NAME/KEY: MOD_RES
<222> LOCATION: (15)..(15)
<223> OTHER INFORMATION: Aspartic acid or glutamic acid
<220> FEATURE:
<221> NAME/KEY: MOD_RES
<222> LOCATION: (16)..(16)
<223> OTHER INFORMATION: Glutamic acid, alpha-methyl-glutamic acid or
      not present
<220> FEATURE:
<221> NAME/KEY: MOD_RES
<222> LOCATION: (17)..(17)
<223> OTHER INFORMATION: Glutamine, glutamic acid, lysine, arginine or
      not present
<220> FEATURE:
<221> NAME/KEY: MOD_RES
<222> LOCATION: (18)..(18)
<223> OTHER INFORMATION: Alanine, arginine or not present

```
<220> FEATURE:
<221> NAME/KEY: MOD_RES
<222> LOCATION: (19)..(19)
<223> OTHER INFORMATION: Alanine, valine or not present
<220> FEATURE:
<221> NAME/KEY: MOD_RES
<222> LOCATION: (20)..(20)
<223> OTHER INFORMATION: Lysine, glutamine, arginine, alpha-methyl-
      glutamic acid or not present
<220> FEATURE:
<221> NAME/KEY: MOD_RES
<222> LOCATION: (21)..(21)
<223> OTHER INFORMATION: Aspartic acid, glutamic acid, leucine or not
      present
<220> FEATURE:
<221> NAME/KEY: MISC_FEATURE
<222> LOCATION: (22)..(22)
<223> OTHER INFORMATION: May or may not be present
<220> FEATURE:
<221> NAME/KEY: MOD_RES
<222> LOCATION: (23)..(23)
<223> OTHER INFORMATION: Isoleucine, valine or not present
<220> FEATURE:
<221> NAME/KEY: MOD_RES
<222> LOCATION: (24)..(24)
<223> OTHER INFORMATION: Alanine, cysteine, glutamic acid, glutamine,
      alpha-methyl-glutamic acid or not present
<220> FEATURE:
<221> NAME/KEY: MISC_FEATURE
<222> LOCATION: (25)..(25)
<223> OTHER INFORMATION: May or may not be present
<220> FEATURE:
<221> NAME/KEY: MOD_RES
<222> LOCATION: (26)..(26)
<223> OTHER INFORMATION: Alanine, isoleucine, leucine, valine or not
      present
<220> FEATURE:
<221> NAME/KEY: MOD_RES
<222> LOCATION: (27)..(27)
<223> OTHER INFORMATION: Alanine, lysine, methionine, arginine or not
      present
<220> FEATURE:
<221> NAME/KEY: MISC_FEATURE
<222> LOCATION: (28)..(29)
<223> OTHER INFORMATION: May or may not be present
<220> FEATURE:
<221> NAME/KEY: MOD_RES
<222> LOCATION: (30)..(30)
<223> OTHER INFORMATION: Cysteine, lysine or not present
<220> FEATURE:
<221> NAME/KEY: MISC_FEATURE
<222> LOCATION: (31)..(40)
<223> OTHER INFORMATION: This region may encompass 2 to 10 residues,
      wherein some positions may not be present
<220> FEATURE:
<221> NAME/KEY: MISC_FEATURE
<222> LOCATION: (41)..(60)
<223> OTHER INFORMATION: This region may encompass 8 to 20 amino acids
      including "KRNRNNIA" or "GPSSGAPPPS" or "GPSSGAPPPSK" or
      "HSQGTFTSDYSKYLD" or "HSQGTFTSDYSRYLDK" or "HGEGTFTSDLSKQMEEEAVK,"
      wherein some or all positions may be absent
<220> FEATURE:
<223> OTHER INFORMATION: See specification as filed for detailed
      description of substitutions and preferred embodiments

<400> SEQUENCE: 59

Xaa Xaa Xaa Gly Thr Phe Thr Ser Asp Xaa Xaa Xaa Xaa Xaa Xaa
 1               5                  10                  15

Xaa Xaa Xaa Xaa Xaa Phe Xaa Xaa Trp Xaa Xaa Asn Thr Xaa Gly Gly
             20                  25                  30

Gly Gly Gly Gly Gly Gly Gly Gly Xaa Xaa Xaa Xaa Xaa Xaa Xaa
             35                  40                  45

Xaa Xaa Xaa Xaa Xaa Xaa Xaa Xaa Xaa Xaa Xaa Xaa
         50                  55                  60
```